(12) United States Patent
Atallah et al.

(10) Patent No.: US 9,486,568 B2
(45) Date of Patent: Nov. 8, 2016

(54) FUZZY LOGIC

(71) Applicant: B. BRAUN AVITUM AG, Melsungen (DE)

(72) Inventors: Richard Atallah, Melsungen (DE); Christof Strohhoefer, Kassel (DE); Juergen Wagner, Kassel (DE)

(73) Assignee: B. BRAUN AVITUM AG, Melsungen (DE)

( * ) Notice: Subject to any disclaimer, the term of this patent is extended or adjusted under 35 U.S.C. 154(b) by 421 days.

(21) Appl. No.: 14/190,782

(22) Filed: Feb. 26, 2014

(65) Prior Publication Data

US 2014/0323942 A1    Oct. 30, 2014

(30) Foreign Application Priority Data

Feb. 28, 2013   (DE) .......................... 10 2013 101 989

(51) Int. Cl.
*A61M 1/16* (2006.01)
*A61M 1/34* (2006.01)
(Continued)

(52) U.S. Cl.
CPC ............ *A61M 1/3403* (2014.02); *A61B 5/021* (2013.01); *A61M 1/16* (2013.01); *A61M 1/1613* (2014.02);
(Continued)

(58) Field of Classification Search
CPC .... A61B 3/02; A61B 3/024; A61B 3/14535; A61B 3/14551; A61B 5/02; A61B 5/021; A61B 5/024; A61M 1/16; A61M 1/1613; A61M 1/34; A61M 1/3403; A61M 1/341; A61M 1/3639; A61M 2205/3303; A61M 2205/3341; A61M 2205/3344; A61M 2205/50; A61M 2205/52; A61M 2230/005; A61M 2230/30; B01D 17/12; B01D 61/22; B01D 61/32; B01D 2311/10; B01D 2311/12; B01D 2311/14; B01D 2311/16; B01D 2311/165; G05B 13/0275; G05B 13/0285; G05B 13/0295; G06N 3/0436; G06N 5/048; G06N 7/02; G06N 7/023; G06N 7/04; G06N 7/046

USPC ......... 210/85, 90, 96.2, 97, 137, 143, 321.6, 210/637, 645, 646, 739, 741; 604/4.01, 604/5.01, 65–67; 700/50, 273, 282; 702/45, 702/50, 139, 189; 706/52, 900

See application file for complete search history.

(56) References Cited

U.S. PATENT DOCUMENTS 5,465,320 A * 11/1995 Enbutsu ............. G05B 13/0285
                                                          706/23
5,503,624 A    4/1996 Roeher et al.
(Continued)

FOREIGN PATENT DOCUMENTS

DE    198 21 534    8/1999
DE    100 47 421    1/2003
(Continued)

OTHER PUBLICATIONS

German Search Report for DE 10 2013 101 989.7 issued Nov. 18, 2013.
(Continued)

*Primary Examiner* — Joseph Drodge
(74) *Attorney, Agent, or Firm* — RatnerPrestia

(57) ABSTRACT

The described system and method for blood treatment are configured to detect at least two hemodynamic parameters, for example the blood pressure and the relative blood volume, during the blood treatment. At least two fuzzy modules receive measuring values of the hemodynamic parameters as input variables, wherein the output signals transmitted by the fuzzy modules are weighted by at least one weighting module. A setting means effectuates setting of at least one variable, for example an ultrafiltration rate, a dialysis fluid conductivity or a dialysis fluid temperature, in response to the output signal transmitted by the weighting module. In this way, e.g. threatening intradialytic hypotensive episodes can be detected and avoided. The system can be designed as a dialyzer for hemodialysis, hemofiltration or hemodiafiltration.

8 Claims, 20 Drawing Sheets

(51) Int. Cl.
  B01D 61/22    (2006.01)
  B01D 61/32    (2006.01)
  A61B 5/02     (2006.01)
  A61B 5/021    (2006.01)
  A61M 1/36     (2006.01)
  A61B 5/024    (2006.01)
  A61B 5/145    (2006.01)
  A61B 5/1455   (2006.01)

(52) U.S. Cl.
  CPC .......... *A61M 1/3639* (2013.01); *B01D 61/32* (2013.01); *A61B 5/02* (2013.01); *A61B 5/024* (2013.01); *A61B 5/14535* (2013.01); *A61B 5/14551* (2013.01); *A61M 2205/3303* (2013.01); *A61M 2205/3341* (2013.01); *A61M 2205/3344* (2013.01); *A61M 2205/50* (2013.01); *A61M 2205/52* (2013.01); *A61M 2230/005* (2013.01); *A61M 2230/30* (2013.01); *B01D 61/22* (2013.01)

(56) References Cited

U.S. PATENT DOCUMENTS

| | | | | |
|---|---|---|---|---|
| 5,655,056 | A * | 8/1997 | Tasaka | G06N 7/04 700/2 |
| 5,988,844 | A * | 11/1999 | Timm | G06N 7/023 700/2 |
| 6,423,022 | B1 | 7/2002 | Roeher et al. | |
| 6,579,241 | B2 | 6/2003 | Roeher | |
| 6,780,322 | B1 * | 8/2004 | Bissler | A61M 1/16 210/103 |
| 7,769,474 | B2 * | 8/2010 | Fregene | G05B 13/0275 244/234 |
| 7,785,463 | B2 | 8/2010 | Bissler et al. | |
| 2002/0068015 | A1 | 6/2002 | Polaschegg et al. | |
| 2009/0112102 | A1 | 4/2009 | Roeher et al. | |
| 2010/0016776 | A1 | 1/2010 | Roeher et al. | |
| 2011/0036773 | A1 | 2/2011 | Moissl et al. | |
| 2011/0137173 | A1 * | 6/2011 | Lowe | A61B 5/02152 600/454 |
| 2011/0163034 | A1 | 7/2011 | Castellarnau | |
| 2012/0123234 | A1 * | 5/2012 | Atlas | A61B 5/7264 600/365 |
| 2013/0080376 | A1 * | 3/2013 | Yao | G06N 3/0436 706/52 |
| 2013/0103630 | A1 * | 4/2013 | Yao | G06N 3/0436 706/47 |
| 2013/0211602 | A1 * | 8/2013 | Scheu | G05B 11/01 700/282 |
| 2014/0201126 | A1 * | 7/2014 | Zadeh | G06K 9/627 706/52 |

FOREIGN PATENT DOCUMENTS

| | | |
|---|---|---|
| DE | 10 2008 010 531 | 8/2009 |
| EP | 0 661 065 | 7/1995 |
| EP | 0 956 872 | 11/1999 |
| EP | 1226838 | 7/2002 |
| EP | 1 514 562 | 3/2005 |
| EP | 1 844 800 | 10/2007 |
| EP | 1 900 384 | 3/2008 |
| WO | WO 00/66197 | 11/2000 |

OTHER PUBLICATIONS

European Search Report for EP 14 15 6854 issued Jun. 26, 2014.
Ahmad Taher Azar, "Biofeedback Systems and Adaptive Control Hemodialysis Treatment," Saudi J Kidney Dis Transplant Nov. 2008; 19(6); ISSN: 1319-2442.
Schmidt et al., "Prevention of haemodialysis-induced hypotension by biofeedback control of ultrafiltration and infusion," Nephrol Dial Transplant Mar. 2001.
Nordio et al., "Projection and simulation results of an adaptive fuzzy control module for blood pressure and blook volume during demodialysis," Asaio Journal, Jul. 1994, pp. 686-690. XP000498259.

* cited by examiner

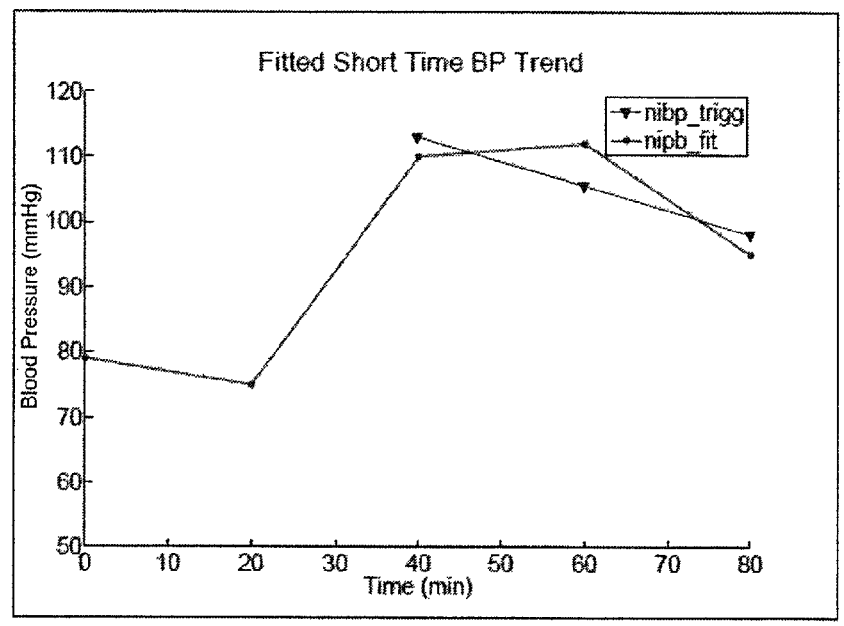
(a)
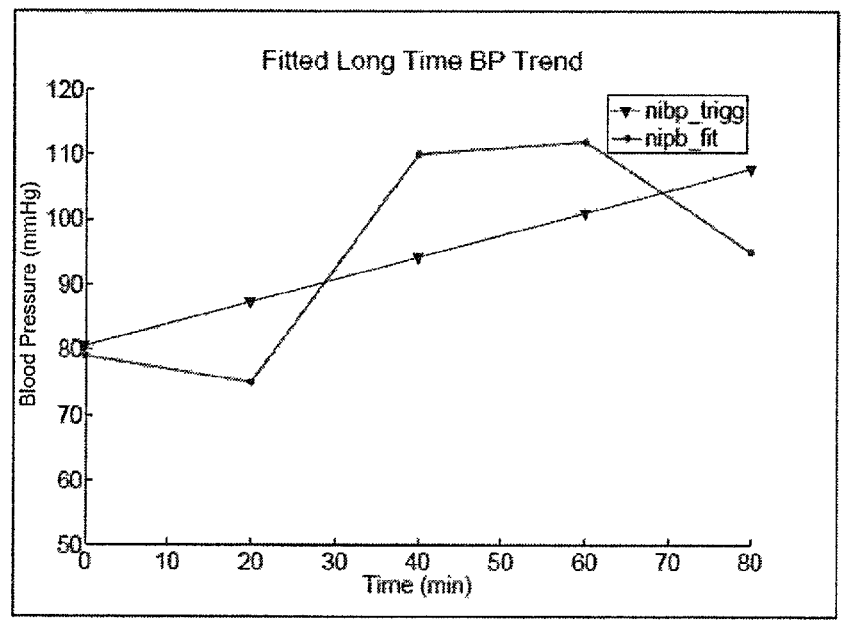
(b)
Fig. 3

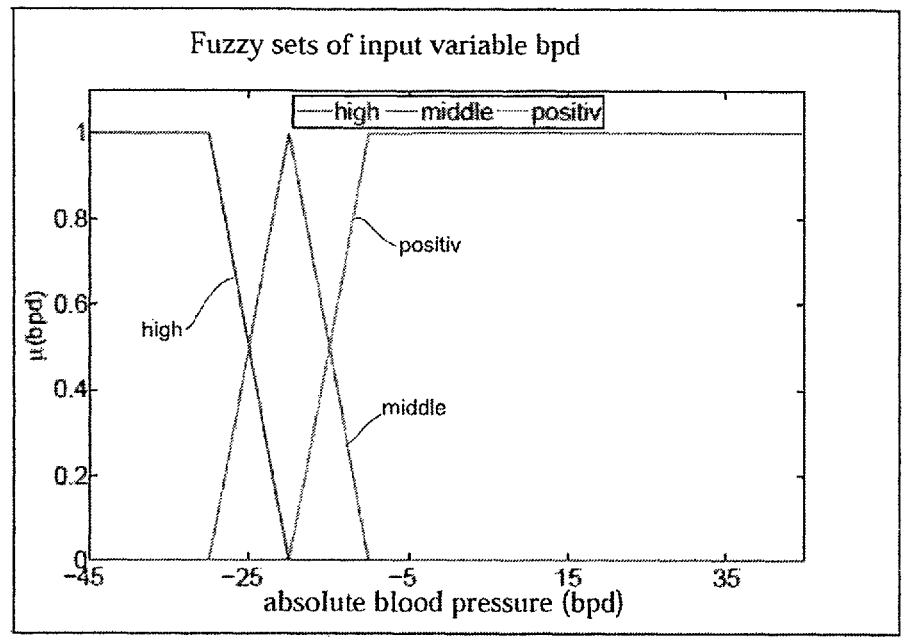
(a)
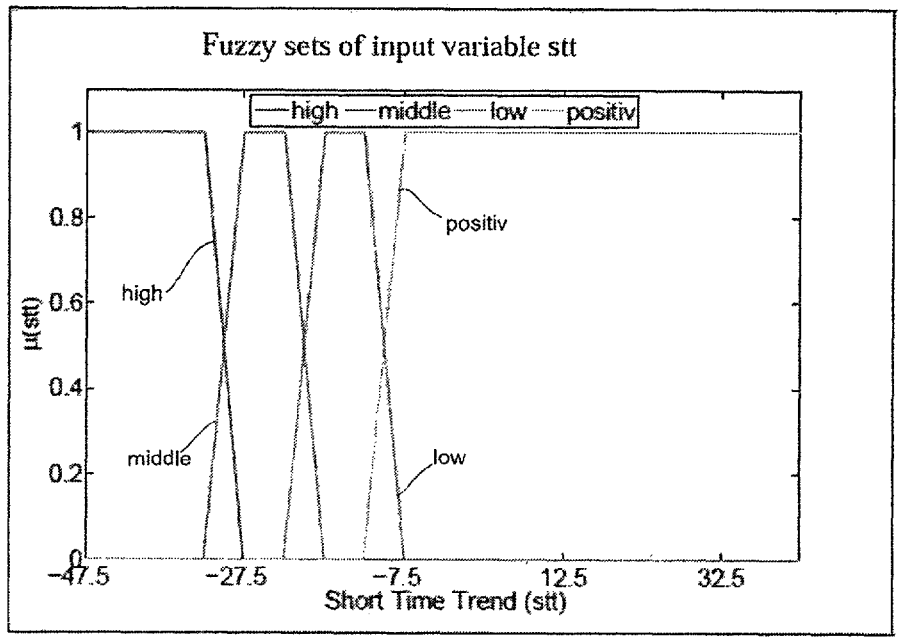
(b)
Fig. 4

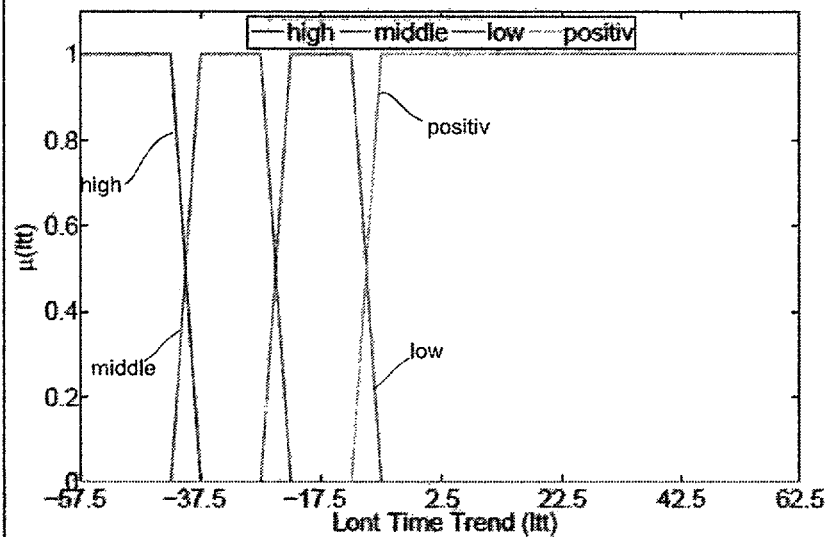
(c)
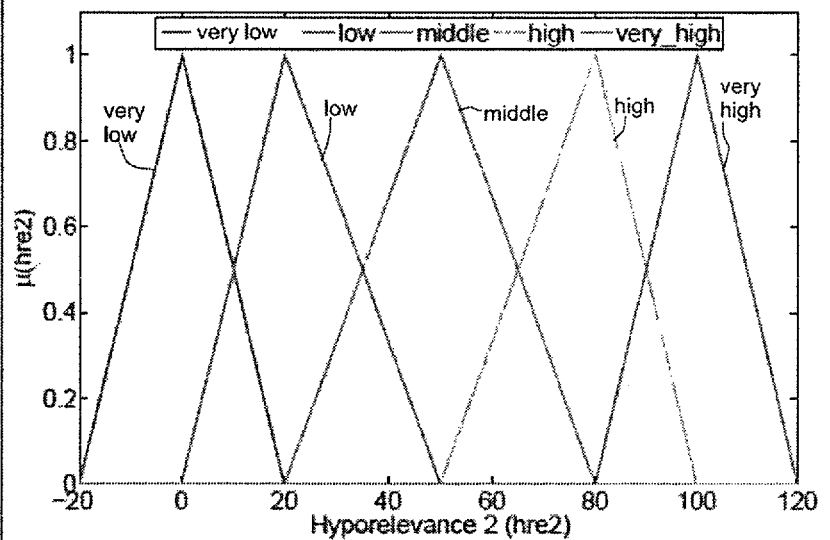
(d)
Fig. 4

Fig. 12: Further embodiment of the system

FUZZY LOGIC

CROSS REFERENCE TO RELATED APPLICATIONS

This application claims priority to German application DE 10 2013 101 989.7 filed Feb. 28, 2013, the contents of such application being incorporated by reference herein.

FIELD OF THE INVENTION

The invention relates to a system and a method adapted to be used for blood treatment, e.g. hemodialysis, hemofiltration or hemodiafiltration.

BACKGROUND OF THE INVENTION

Intradialytic hypotensive episodes, IHE, are among the most frequently occurring complications during dialysis treatment. Intradialytic hypotension can frequently be triggered by rapid liquid withdrawal or incorrectly determined dry weight. A typical reason can be strong reduction of the central blood volume and an inadequate response to such reduction. Numerous algorithms and methods for avoiding such hypotensions have been developed so far. However, it has not been possible to completely avoid intradialytic hypotensive episodes.

From EP 0 956 872 A2 a system of a physiological control loop based on blood pressure comprising a fuzzy controller is known which evaluates blood pressure input values in real time and appropriately sets the ultrafiltration (UF) rate.

When for avoiding intradialytic morbidities by incorporating a physiological control loop a hemodynamic parameter, e.g. either the blood pressure BP or the relative blood volume RBV is controlled, detrimental effects may occur. One drawback of controlling the blood pressure is the patient's impaired well-being due to the large number of blood pressure measurements by means of a cuff. Although the reduction of the number of blood pressure measurements for each therapy solves the problem of frequent blood pressure measurements, another problem is caused, however, as the patient's blood pressure remains unmonitored over rather long periods of time. The relative blood volume can be measured with the aid of an external sensor or a sensor built in the dialyser (e.g. hematocrit sensor) at very short time intervals (<1 s) without any loss of the patient's comfort. Although the relative blood volume is continuously controlled, no correlation to the predialytic, postdialytic and intradialytic blood pressure is shown. Other examinations resulted in the fact that by controlling the relative blood volume a reduction of hypotensive episodes up to 30% can be reached.

SUMMARY OF THE INVENTION

It is an object of this invention to reduce morbidities due to blood treatment, e.g. intradialytic morbidities, inter alia intradialytic hypotensive episodes.

In one, several or all embodiments a newly developed physiological control loop is provided which evaluates, weights and controls with the aid of a physiological control loop at least two physiological parameters of the patient's condition. In one, several or all embodiments the UF rate is appropriately given as a variable. The two concrete physiological parameters can be e.g. the blood pressure and the relative blood volume. However, alternatively or additionally also other relevant parameters, e.g. the oxygen saturation of the blood, the heart rate etc. can equally be incorporated in the control.

In one, several or all embodiments morbidities due to blood treatment, e.g. intradialytic morbidities, inter alia intradialytic hypotensive episodes, are avoided or at least reduced by an expert physiological control loop.

According to an aspect of the invention, a method or system for blood treatment is provided which is configured to detect at least two hemodynamic parameters, for example blood pressure and relative blood volume, during the blood treatment, wherein at least two fuzzy modules receiving measured values of the hemodynamic parameters as input parameters, at least one weighting module to which at least two of the output signals transmitted by the fuzzy modules can be supplied, and at least one setting means for setting at least one variable, for instance an ultrafiltration rate, UFR or UF rate, a dialysis fluid conductivity or a dialysis fluid temperature, in response to an output signal transmitted by the weighting module are provided.

The method or system can be configured for detecting or avoiding intradialytic hypotensive episodes, the monitored hemodynamic parameters being adapted to comprise two or more of the following parameters:

Blood pressure, course of the blood pressure, relative blood volume, course of the relative blood volume, hematocrit value, hematocrit course, oxygen saturation, course of oxygen saturation of the blood, heart rate, course of the heart rate, absorbance or course of absorbance of uremic toxins or similar hemodynamic parameters, or further physical parameters such as blood pressure values measured by the system such as arterial and/or venous blood pressure and/or the courses thereof.

The system can be designed as dialyser for hemodialysis, hemofiltration or hemodiafiltration. The method equally can be designed for hemodialysis, hemofiltration or hemodiafiltration.

The method or system can be configured to discontinuously measure the blood pressure values at particular time intervals, to compare them to a limit and, in the case of decrease of the blood pressure value below the limit, to change to continuous blood pressure measurement.

For example a short-time fuzzy module, STFM, can be provided which is configured to evaluate the behavior of the blood pressure in an earlier period of time and to compute a variable reflecting the patient's condition by way of evaluating rules.

Alternatively or additionally, a long-time fuzzy module, LTFM, can be provided by which the course of the blood pressure is evaluated over a rather long period of time which can be longer than the period of time evaluated by the afore-mentioned fuzzy module (short-time fuzzy module).

In the method or system a measuring unit in the form of a hemosensor and another fuzzy module for evaluating the measuring signal transmitted by the hemosensor can be provided, wherein e.g. the blood volume and the course of the blood volume of a patient can be evaluated. The hemosensor can be e.g. a hematocrit sensor or else a hemoglobin sensor or an oxygen saturation sensor or a different form of a sensor detecting one or more blood parameters. The hemosensor can detect e.g. one or more of the following hemodynamic parameters: blood pressure, course of blood pressure, relative blood volume, course of relative blood volume, hematocrit value, hematocrit course, oxygen saturation, course of oxygen saturation of the blood, heart rate, course of heart rate, absorbance of uremic toxins or similar hemodynamic parameters or hemodynamic courses, or further physical parameters or physical courses such as blood pressure values measured by the system such as arterial and/or venous blood pressure and, resp., the course of arterial and/or venous blood pressure. Said sensors are referred to as hemosensors.

Optionally at least two or three of the fuzzy modules can form a respective output value (hre1, hre2, hre3) constituting a hypotonic relevance, hereinafter referred to as hyporelevance, wherein a weighting module can be configured to combine the hyporelevance output values formed by the fuzzy modules into a resulting hyporelevance output value. Another fuzzy module can evaluate e.g. the resulting hyporelevance output value together with a relative ultrafiltration volume describing the ratio between the current and the total ultrafiltration volumes and can compute a corresponding desired ultrafiltration rate.

In one, several or all embodiments at least two or three of the fuzzy modules can form a respective output value representing a hyporelevance, the weighting module being configured to combine the hyporelevance output values formed by the fuzzy modules into a resulting hyporelevance output value, and comprising a further fuzzy module that evaluates the resulting hyporelevance output value together with a relative ultrafiltration volume, which describes the ratio between the current and the total ultrafiltration volume, or the relative time, which describes the ratio of the current and the total time, and computes a corresponding desired ultrafiltration rate.

In the method or system the relative course of blood volume RBV can be stored in the form of a RBV curve, the RBV curve with different window sizes can be approached by an algorithm, for example a least square algorithm, and the course of blood volume can be monitored at time intervals corresponding to a window size for which sufficient overlapping of e.g. 50% or more is resulting in the actual course of blood volume.

BRIEF DESCRIPTION OF THE DRAWINGS

The invention is best understood from the following detailed description when read in connection with the accompanying drawings. Included in the drawings are the following figures:

FIG. 3 shows diagrams for a linear least square fit approach of the blood pressure, FIG. 4 illustrates fuzzy sets of input variables and an output variable of an LTFM.

DETAILED DESCRIPTION OF PREFERRED EMBODIMENTS

In one, several or all embodiments a physiological control loop is provided which is monitoring plural physiological parameters reflecting the condition of the patient during his/her dialysis treatment. By way of the findings obtained from these parameters in one, several or all embodiments intradialytic morbidities, inter alia hypotensive episodes, are recognized early. The prevention and, resp., elimination thereof is achieved by adapting variables which contribute to preventing hypotensive episodes in good time.

As an example of said physiological parameters in one, several or all embodiments of the invention the blood pressure (BP) and the relative blood volume (RBV) are considered. The variable is realized, for example, in the form of the ultrafiltration rate (UF rate).

The physiological control loop consists in one, several or all embodiments of one or more, e.g. two, measuring units and one or more, e.g. five, evaluating units. A first measuring unit in one, several or all embodiments is a blood pressure measurement module for monitoring the blood pressure, i.e. blood pressure values, hereinafter also referred to as BP or BP values, at different time intervals. The second measuring unit in one, several or all embodiments is a hematocrit sensor for continuously monitoring the relative blood volume of the patient. One or two of the evaluating units evaluate the behavior of the blood pressure, where each unit outputs a value that describes the patient's condition. An e.g. third evaluating unit evaluates the behavior of the relative blood volume and equally computes a value that describes the patient's condition. Said computed values are weighted in one, several or all embodiments in a fourth evaluating unit which combines the three status values into a resulting value. Said resulting value is evaluated by a fifth evaluating unit that computes a corresponding UF rate.

All evaluating units, or all except one, can be fuzzy modules evaluating linguistic variables (input variables). The one remaining evaluating unit, which not designed as fuzzy module, can be for example a weighting unit that combines the status values into a resulting value.

Figure 1:
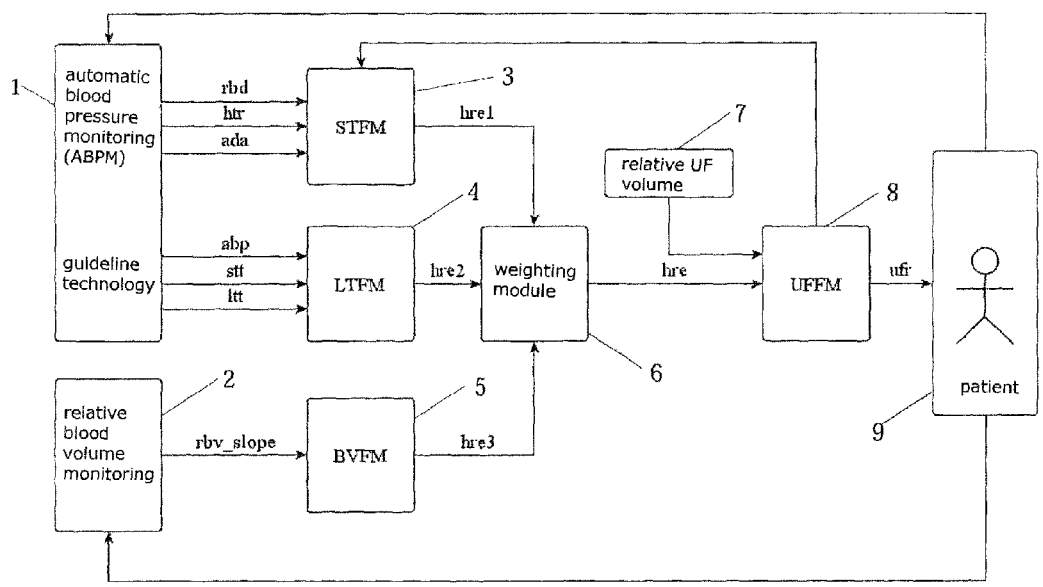
FIG. 1 shows an embodiment according to the invention of a physiological control loop.
Figure 2:
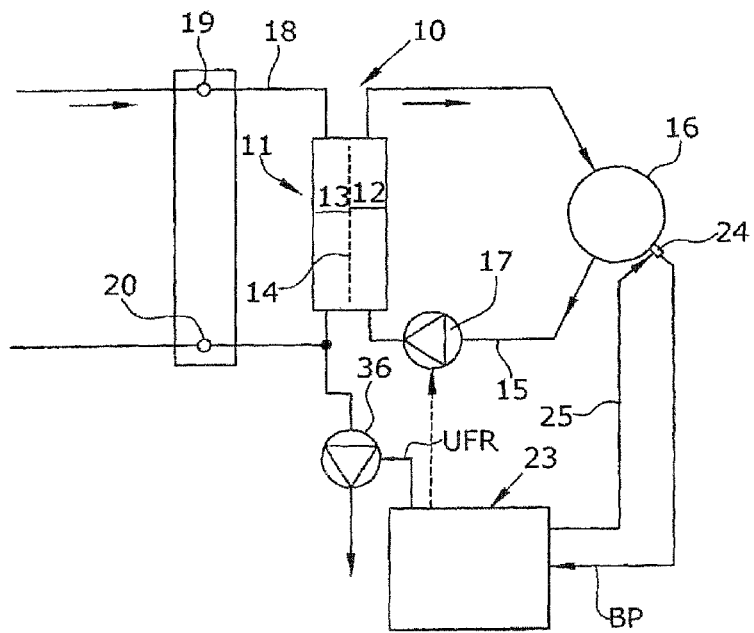
FIG. 2 shows an embodiment of a dialyser.

FIG. 1 represents a diagram of an embodiment of the physiological control loop. As described above, an automatic blood pressure measuring and monitoring means ("Automatic Blood Pressure Measurement ABPM") 1, possibly together with a guideline technology as described e.g. in EP 1226838A2, supplies continuously, e.g. at intervals of 5 minutes for instance (or longer or shorter), blood pressure values, also referred to as BP or BP values here, from a storage unit which can be e.g. an internal or external hard disk of the automatic blood pressure detecting module 1 or of the system. These values consist of computed and currently measured BP values that can be measured discontinuously or continuously. Continuous measurement is performed as soon as the currently measured BP value falls below a predefined limit. The continuous blood pressure measurement is further performed as long as the currently measured blood pressure remains below a predefined limit. A first fuzzy module 3 in the form of a short time fuzzy module (STFM) receives from the means 1 three input variables rbd, htr and ada originating from the measured and computed BP values. By way of said variables in a fuzzy inference system (cf. FIG. 13) the behavior of the blood pressure in the earlier period of time, e.g. in the past 30 minutes, is evaluated. The STFM 3 consists e.g. of 48 rules that are evaluated to compute a variable reflecting the patient's condition. Said variable is referred to as hyporelevance one (hre1).

A second fuzzy module 4, which is a long time fuzzy module LTFM, in turn receives from the means (ABPM) 1 and possibly from the storage unit e.g. three input variables bpd, stt and ltt which only consist of the measured BP values. Said variables bpd, stt and ltt evaluate the behavior of the blood pressure within e.g. the past 120 minutes in a fuzzy inference system, for example. The variable bpd is a BP difference of the two last measured BP values, for example. The variable stt is the difference e.g. of the last and the last but three BP values fitted with a linear fit. The variable ltt is the difference e.g. of the last and the last but five BP values fitted with a linear fit. Said three variables are evaluated in the LTFM by the fuzzy sets and the corresponding rules thereof in a fuzzy inference system (cf. FIG. 13). In so doing, a new status variable is computed, viz. hyporelevance two (hre2).

Since inflating the BP cuff is very uncomfortable to the patient, the blood pressure cannot be monitored at shorter time intervals. Therefore a so called guideline technology is used in which the blood pressure is computed based on the patient's own stored BP courses and is applied to the current therapy.

As in each prognosis system there is an inaccuracy in the computed prognosis items, in this case in the computed BP values. Such inaccuracy can be reduced by a second measuring unit, i.e. the hematocrit sensor. For this reason, a third fuzzy module 5, the blood volume fuzzy module BVFM, is employed which receives its input variable from a blood volume measuring and monitoring means 2 detecting the relative blood volume and interprets the course of relative blood volume of the patient 9. At intervals of e.g. 10 minutes with 50% overlapping, the blood volume curve the coordinates of which are stored in the storage unit are evaluated in real time e.g. in a fuzzy inference system (cf. FIG. 19). Said evaluation is expressed in the form of a third status variable, viz. hyporelevance three (hre3).

The measuring and monitoring means 1, 2 are connected to a patient 9, as is shown in FIG. 1.

The three hyporelevances hre1, 2, 3 formed by the three fuzzy modules are combined in a weighting unit 6 into a resulting hyporelevance (hre).

The final hyporelevance hre indicative of a threatening too low blood pressure is evaluated together with the relative UF volume originating from a block 7 and describing the ratio of the current and the total UF volume in a fourth fuzzy module (UFFM) 8 which computes a corresponding UF rate at this point.

In one, several or all embodiments of the invention a physiological control loop comprising at least two control parameters is used. For blood treatment, e.g. dialysis, in the physiological control loop two or more patient parameters are applied as control variables, e.g. the blood pressure and the relative blood volume. In this case two or more parameters from two or more different sensors are controlled. In the shown embodiment of the physiological control loop two hemodynamic parameters, i.e. the blood pressure and the relative blood volume, are controlled.

In one, several or all embodiments the physiological control loop has a modular design and in the shown embodiment it includes five modules: three input modules 3 to 5, an intermediate module 6 and an output module 8. The three input modules are the BP fuzzy modules 3, 4 (LTFM and STFM) evaluating the long-time behavior and the short-time behavior of the BP and the blood volume fuzzy module 5 (BVFM) evaluating the RBV course of the patient 9. Each of said three modules 3 to 5 computes an evaluating variable that provides information about the behavior of the hemodynamic control variables reflecting the patient's condition.

In the fourth module 6, the weighting module, the three evaluating variables produced from the first three input modules 3 to 5 are combined into a final evaluating variable hre.

The fifth module 8 evaluates the final evaluating variable mainly together with a variable that provides information about the residual UF volume, wherein the UF rate is computed.

In one, several or all embodiments an indirect weighting of the control parameters can be performed.

For reasons of the patient's comfort the blood pressure should not be measured at shorter time intervals. During the time when no BP values are measured the guideline technology ensures that computed BP values originating from the patient's own BP values from former therapies are applied to the current therapy. As in each prognosis system there is an inaccuracy in the computed prognosis items, in this case in the computed BP values. This inaccuracy can be reduced by the second measuring unit, viz. the hematocrit sensor. During the time when the BP values are computed, the information from the hematocrit sensor and from the computed BP values are weighted at different percentages so that insignificant information is devaluated by lower weighting and significant information is revaluated by high weighting.

Due to the modular structure the physiological control loop can be extended at will so that further physiological parameters can be easily incorporated. Input modules for any measuring variables can be added. Each of these input modules outputs a hyporelevance. Said hyporelevances are combined in the intermediate module 6 into an overall hyporelevance either based on predetermined conditions or based on corresponding fuzzy sets. The setting of the variable realized in the fuzzy module 8 is then based on this overall hyporelevance. Moreover, also the use of different variables is possible. They are either provided on the basis of the hyporelevance computed by the single intermediate module 6 or different hyporelevances which are then used for setting a respective variable are computed by plural intermediate modules.

Based on the modular structure of this physiological control loop, further hemodynamic parameters can be incorporated in the system as independent modules. These can be, e.g. the oxygen saturation, the heart rate, the absorbance of uremic toxins or similar hemodynamic parameters. In addition to or instead of the UF rate, the dialysis fluid temperature, the dialysis fluid conductivity or similar parameters can be used as variables.

Apart from the hemodynamic parameters, also further physical parameters such as the BP values such as the arterial and the venous blood pressure measured in the machine can be incorporated.

Due to the monitoring and control of patient parameters by plural hemodynamic sensors which provide information about the stability of the patient's circulatory system, great well-being of the patient during dialysis can be reached. This is reflected, on the one hand, in a reduction of the hypotensive episodes during dialysis and, on the other hand, in the patient's increased comfort due to a reduction of BP measurements by means of a cuff.

In one or more embodiments there exists also the possibility of continuous blood pressure measurement. In such case a fuzzy module can be dispensed with, e.g. the module 4.

The physiological control loop has a modular structure in one, several or all embodiments. Hence a modular system having an individual and overall function is created. In this way individual modules can be switched on and off as desired, depending on which input parameters and which sensors are available and which parameter controls are desired by the physician. Further patient parameters can be easily included in the system in a modular way without influencing the functionality of other modules.

By weighting individual pieces of information devaluation of less significant pieces of information and revaluation of more significant pieces of information is obtained. The weighting devaluates information of little significance and revaluates information of high significance.

Hereinafter the individual modules shown in FIG. 1 are described in detail.

The STFM module 3 and the UFFM module 8 are partly described in EP 0 956 872 B1. That description is fully incorporated in the content of disclosure of the present application. In the present physiological control loop the UFFM module 8 is partly modified.

The LTFM module 4 is a fuzzy module which is independent of the other modules and from the ABPM module 1 receives three input variables computed only on the basis of the measured BP values. These are the difference in blood pressure (bpd), the short time trend (stt) and the long time trend (ltt) which evaluate the behavior of the blood pressure within the last period of time of e.g. 120 minutes. bpd is the BP difference of the two last measured BP values (bpd=$BP_i$−$BP_{i-1}$). stt is the difference of the last and the last but three BP values fitted by linear fit (stt=$BP_{fit(i)}$−$BP_{fit(i-2)}$). ltt is the difference of the last and the last but five BP values fitted by linear fit (ltt=$BP_{fit(i)}$−$BP_{fit(i-4)}$). Fitting of the BP values which is necessary for computing the input variables stt and ltt is shown in FIG. 3. stt and ltt are computed from the newly issued blood pressures on the fitting line. FIG. 3 shows the linear least square fit of the blood pressure.

FIG. 3 shows in the left half (curve a) the adapted short time blood pressure trend. The trigger curve is shown by triangular markings, while the measuring curve is indicated by round dots. In the right half of FIG. 3 (curve b) the adapted long time blood pressure trend is shown. The BP values obtained in this way are equally interconnected by linear portions.

The three afore-mentioned variables are evaluated in the LTFM module 4 by the fuzzy sets and the corresponding rules thereof (cf. FIG. 4). To each input variable different linguistic terms are assigned (μ(bpd)={high, middle, positive}, μ(stt)={high, middle, slight, positive}, μ(ltt)={high, middle, slight, positive}). The number of these linguistic variables permits to establish 3*4*4=48 different rules which in turn offer all possible combinations of the behavior of these variables. According to expert knowledge and statistical methods about the distribution of these variables over plural dialysis patients, ranges within which these variables may be provided were formed. Table 2 provides a survey of the characteristics of the input variables. Table 1 shows the characteristic of the LTFM module 4.

TABLE 1

Table 1 Characteristic of LTFM
Long Time Fuzzy Module LTFM 4

| Input variable | Stt | | | |
|---|---|---|---|---|
| Linguistic terms | High | Middle | slight | positive |
| Ranges | [−45 45] | [−30 −15] | [−20 −5] | [−10 45] |
| Functions | Trapezoid | Trapezoid | trapezoid | trapezoid |
| Input variable | Ltt | | | |
| Linguistic terms | High | Middle | slight | positive |
| Ranges | [−60 −40] | [−45 −25] | [−30 −10] | [−15 60] |
| Functions | Trapezoid | Trapezoid | trapezoid | trapezoid |
| Input variable | Bpd | | | |
| Linguistic terms | High | | middle | positive |
| Ranges | [−45 −15] | | [−25 −10] | [15 45] |
| Functions | Trapezoid | | triangle | trapezoid |
| Output variable | hre2 | | | |
| Linguistic terms | very low | low | middle | high | very high |
| Ranges | [−20 20] | [0 50] | [20 80] | [50 100] | [80 120] |
| Functions | Triangle | triangle | triangle | triangle | triangle |

After evaluating these variables in the LTFM module 4, a new status variable, viz. the hyporelevance two (hre2) is computed. The fuzzy sets and the ranges of this status variable were chosen so that in response to small critical variations of the blood pressure a variation of the UF rate takes place with consideration of the fact that reaching the UF volume remains focused. The fuzzy sets of hre2 are shown in FIG. 4. The characteristics thereof are described in table 2. FIG. 4 shows the fuzzy sets of the input variable and the output variable of the LTFM module 4.

The BVFM module 5 in turn is a fuzzy module in which a fuzzy algorithm is implemented which evaluates the course of the relative blood volume. In order to be able to interpret the course of blood volume of the patient during his/her therapy, a large number of dialysis therapies were considered in which the patients were free of hypotensive episodes. In these therapies the relative blood volume was appropriately evaluated based on the hypothesis that the RBV is unremarkable in a therapy with stable condition of the patient.

The medical expertise recommends a decrease of intradialytic blood volume of 5% per hour. However, temporary fluctuations have to be taken into account to conclude the condition of the patient therefrom. For this, first an RBV limit must be defined. To achieve this, a large number of courses of intradialytic blood volume were analyzed. They were collected from therapies carried out with a defined UF profile. The patients were dialyzed at high UF rates at the beginning of dialysis and at low UF rates toward the end of therapy.

Figure 5:
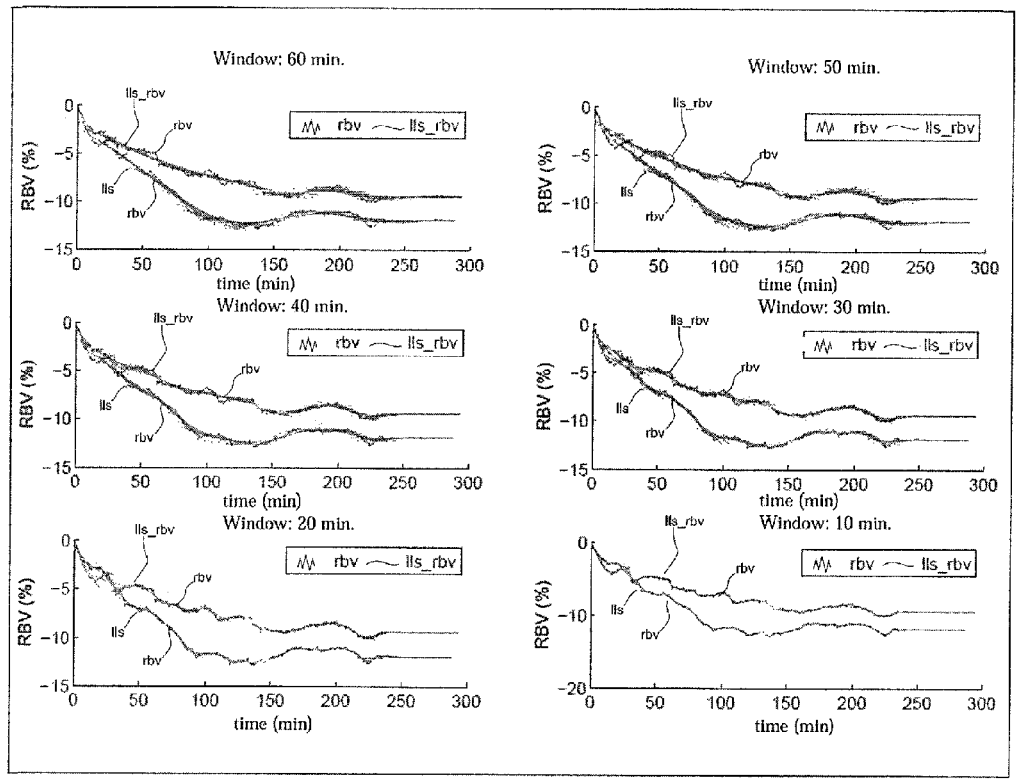
FIG. 5 illustrates fitted RBV curves having different window sizes.

In order to consider temporary fluctuations, the RBV curve has to be disintegrated into small segments. It has to be defined in this context how small the segments should be selected so as to render the RBV curve highly reproducible without losing important information from the curve. For this, the RBV curve was fitted with different window sizes by a linear least square (lls) algorithm. FIG. 5 shows an example of the fit over 6 window sizes (10, 20, 30, 40, 50 and 60 minutes) of two curves of blood volume. The rapidly changing curves in each window plot are courses of blood volume of two patients during a dialysis treatment. The thicker lines changing more slowly are the corresponding fits by an lls algorithm.

FIG. 5 illustrates fitted RBV curves having different window sizes with a width of 10, 20, 30, 40, 50 and 60 minutes. FIG. 5 shows that the best window size which best fits the curve is the window shown at the right bottom with the 10 minutes interval at 50% overlapping. By this overlapping the course of the blood volume can be monitored at short time intervals without losing important information about the behavior of the blood volume. After fitting, the course then can be extrapolated up to one hour and the difference $RBV_{t+60}$ and $RBV_t$ can be formed (cf. the lines as an example in FIG. 5).

Figure 6:
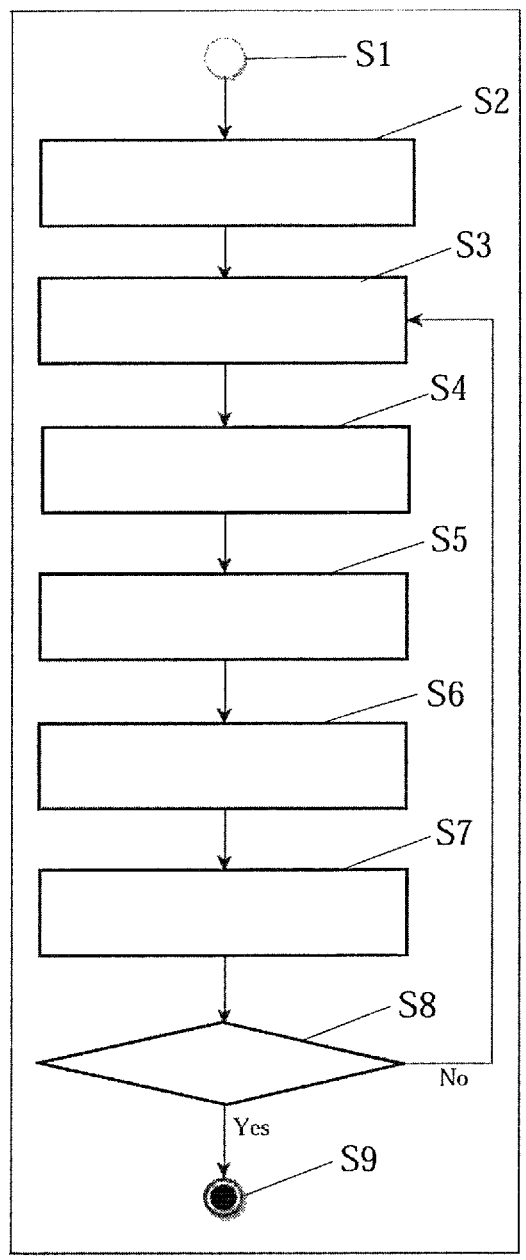
FIG. 6 shows an activity diagram for adapting the RBV at intervals of e.g. 10 minutes.

Next, limits for the blood volume are to be defined. Since RBV curves of stable patients were examined, they can be taken as reference for stable RBV curves and correspondingly the limits can be set. In order to examine within which ranges the blood volume varies in a healthy patient population, the activity diagram described in FIG. 6 was implemented. FIG. 6 shows an activity diagram for fitting the relative blood volume at intervals of 10 minutes.

In the activity diagram shown in FIG. 6 step S1 represents the first step of the adaptation behavior (fitting) which is followed by step S2 in which the values of the relative blood volume obtained for this example during 292 therapy sessions are appropriately assigned in arrays or successively stored. In step 3 the RBV values within the next 10 minutes or every 10 minutes are picked from all arrays built up. In the following step S4 the picked RBV values are adapted at intervals of 10 minutes by means of an lls algorithm ("linear least square" method).

In step S5 subsequently the adapted relative blood volume is extrapolated to one hour. In step S6 then the difference of the first and the last point on the extrapolated line is computed after which in step S7 the median of all computed difference is computed. In step S8 it is finally checked whether all RBV values have been processed. If so, the program ends at a final point S9. Otherwise the program returns to step S3 so that the steps S3 to S8 are passed again.

Figure 7:
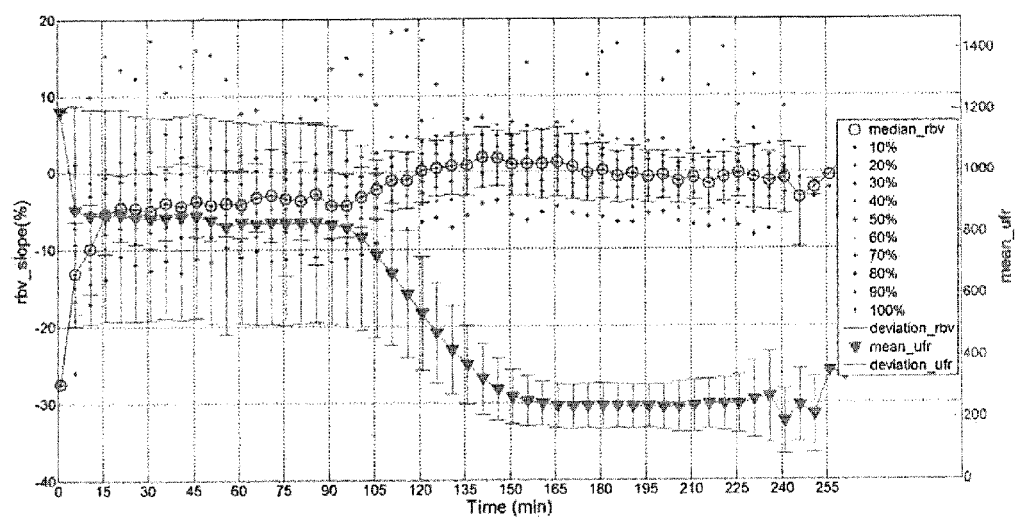
FIG. 7 shows a median of the extrapolated RBV and mean value of UFR in e.g. 292 dialysis therapies.

If the steps are carried out according to FIG. 6, the median course of the RBV values over the therapy as shown in FIG. 7 is obtained. FIG. 7 shows the respective median of the extrapolated RBV value and the mean value of the UF rate during 292 dialysis therapies. The mean values of the UF rates at the fit intervals of the RBV values were computed. These are the triangles in FIG. 7. The stars reflect the percentage affiliations of the RBV vector assorted for forming the median (median is the 50% position in this vector). The error bars around the median values shown as circles are the mean absolute deviations of the median. The error bars around the mean values of the UF rates shown as triangles represent the standard deviations of the UF rates. The high standard deviation in UF rates is caused by the different maximum UF rates for different patients.

As is shown in FIG. 7, three patterns are evident. The first is the course of the median from minute 15 to minute 100. The second pattern is the course of the median from minute 100 to minute 140. The third and last pattern is the course of the median from minute 140 to the end of therapy. For this reason dynamic limits should be set.

It can be hypothetically determined that with a median of −4% the patients show no abnormalities in the course of the blood volume. This can be set as limit. All RBV decreases lying below this limit tend to show an abnormal behavior of the RBV course. In order to tolerate this limit, the lower limit of the mean absolute deviation was taken into account. As also the latter depends on the pattern, it was determined differently for the different patterns. In the first and third patterns the mean value was formed by the mean lower absolute deviation which is −9% for the first pattern and −4% for the third pattern. The limits in the second pattern are dynamic limits and show a linear course. For this reason, in the second pattern dynamic limits of −10% to −4% were formed.

These limits were mirrored in the fuzzy sets. A total of two linguistic terms was defined for the behavior of the relative blood volume, namely μ(rbv)={critical, normal}. The characteristics of these sets are described in the following table 2.

TABLE 2

Table 2 Characteristics of BVFM
Blood volume - Fuzzy Module - SVFF 5

| Input variable | | rbv gradient | |
|---|---|---|---|
| Linguistic terms | | Critical | normal |
| Ranges | pattern 1 | [−20 −4] | [−14 20] |
| | pattern 2 | [−20 . . . 0] | [−14 . . . 20] |
| | pattern 3 | [−20 0] | [−8 20] |
| Function | | Trapezoid | trapezoid |
| Output variable | | hre3 | |
| Linguistic terms | | High | low |
| Ranges | | [0 0.8] | [0.2 1] |
| Function | | Triangle | triangle |

Figure 8:
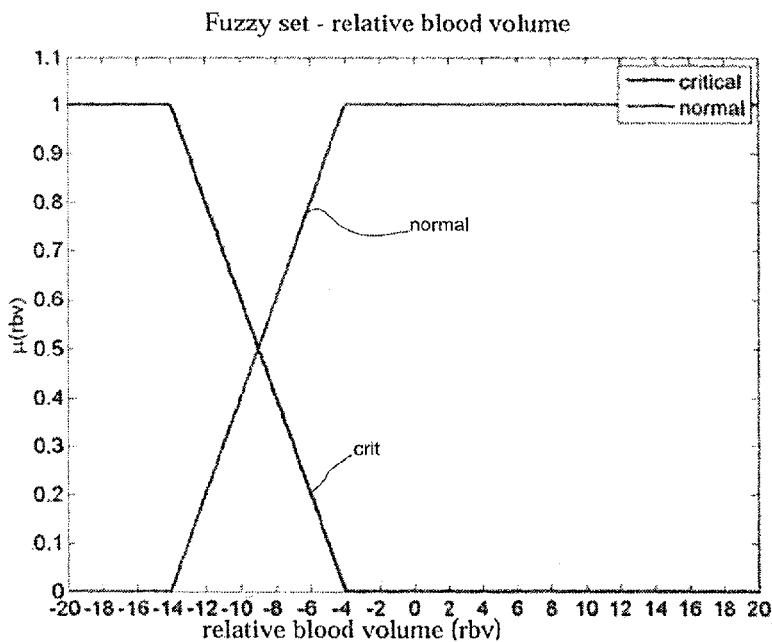
FIGS. 8 to 11 show fuzzy sets for different examples of RBV patterns or hyporelevance.
Figure 9:
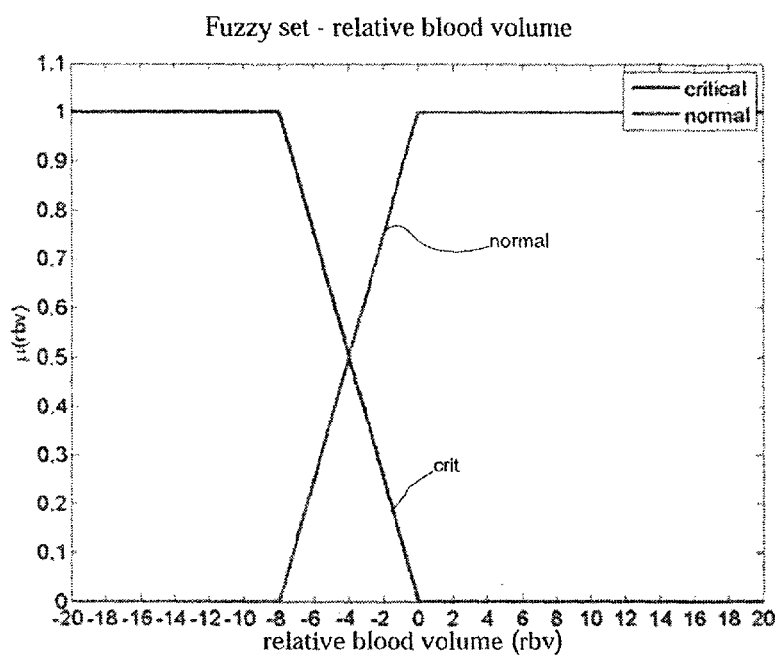
Figure 10:
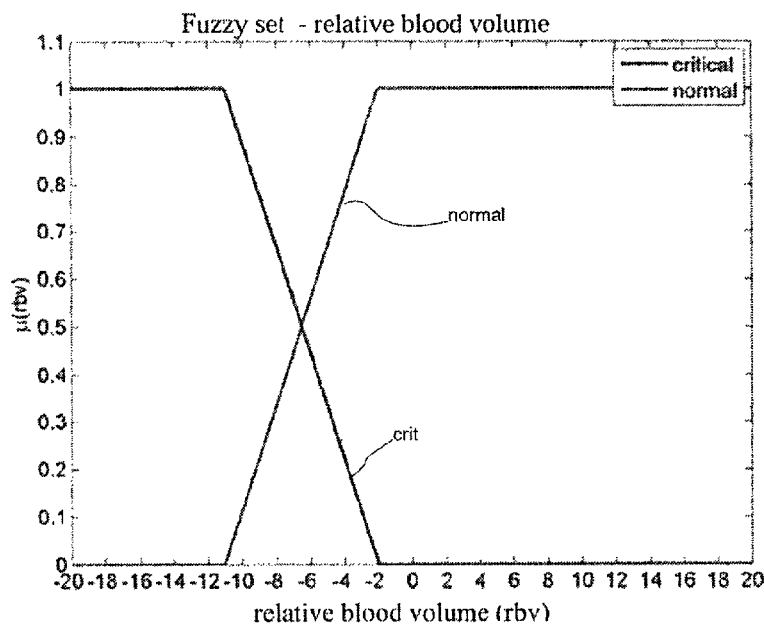

The decrease of the relative blood volume is evaluated in the BVFM module 5 according to the described fuzzy sets and fuzzy rules (cf. FIG. 8, FIG. 9, FIG. 10). As in the other fuzzy modules, a third status variable (hre3), the fuzzy sets and characteristics of which are shown in FIG. 11 and in Table 2 is computed as evaluating variable.

FIG. 8 illustrates fuzzy sets of the RBV pattern 1. FIG. 9 shows one of the fuzzy sets of the RBV pattern 3. FIG. 10 shows the fuzzy sets of the RBV pattern 2. FIG. 11 shows the fuzzy sets of the hre3.

Figure 11:
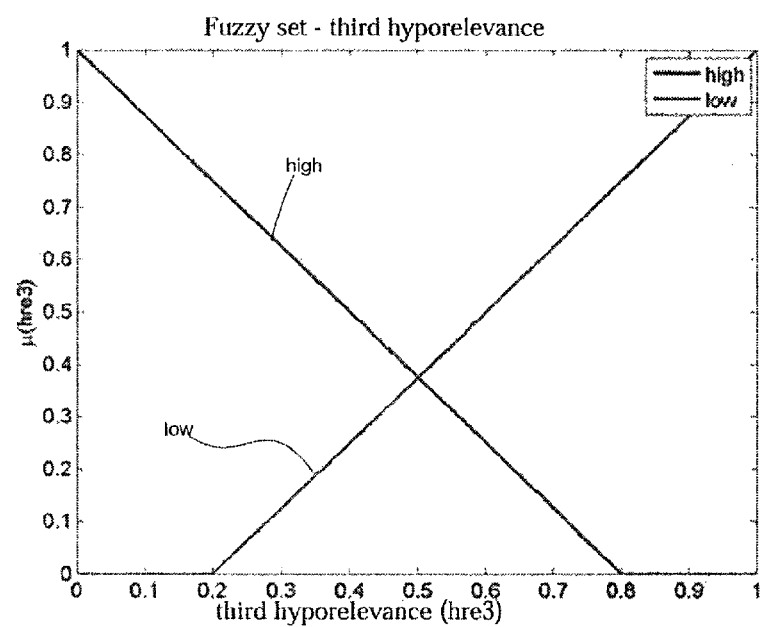

As is visible from FIGS. 8 to 11, a normal course is shown by the curves linearly increasing from 0 to 1 in an oblique manner. The curves decreasing obliquely to the right from 1 to 0, on the other hand, show critical courses by way of which the hyporelevance hre3 shown in FIG. 11 is formed. In this case, too, the curve trace increasing from 0 to 1 to the top right symbolizes an uncritical range of low hyporelevance, whereas the curve trace decreasing from 1 to 0 to the right bottom means high relevance, i.e. represents a critically decreasing blood pressure.

In the weighting unit 6 the evaluation of the individual computed state variables hre1, hre2 and hre3 is performed. The evaluation is a form of combination of all state variables. The weighting unit can be another fuzzy module in which the input variables are assigned to linguistic terms and affiliations. The combination can also be made by scalar weighting of the individual state variables, however.

In so doing, conditions should be determined which take the type of blood pressure (triggered or computed), its significance mirrored by the state variables and the significance of the information obtained from the hematocrit sensor into account.

Further possibilities of extending the system consist in incorporating one or more additional input and/or output parameters. These can be the oxygen saturation, the heart rate and/or the pressures measured by the machine such as the arterial or venous blood pressure. These input parameters are control parameters and can be classified in independent modules. The information of the individual input variables can be evaluated independently in weighting units. As variables, e.g. apart from the UF rate, the dialysis fluid conductivity (LF) and the dialysis fluid temperature (DT)

can be computed in independent fuzzy modules, the dialysis fluid conductivity fuzzy module (DLFM) and the dialysis fluid temperature fuzzy module (DTFM) and can be set in the machine.

Figure 12:
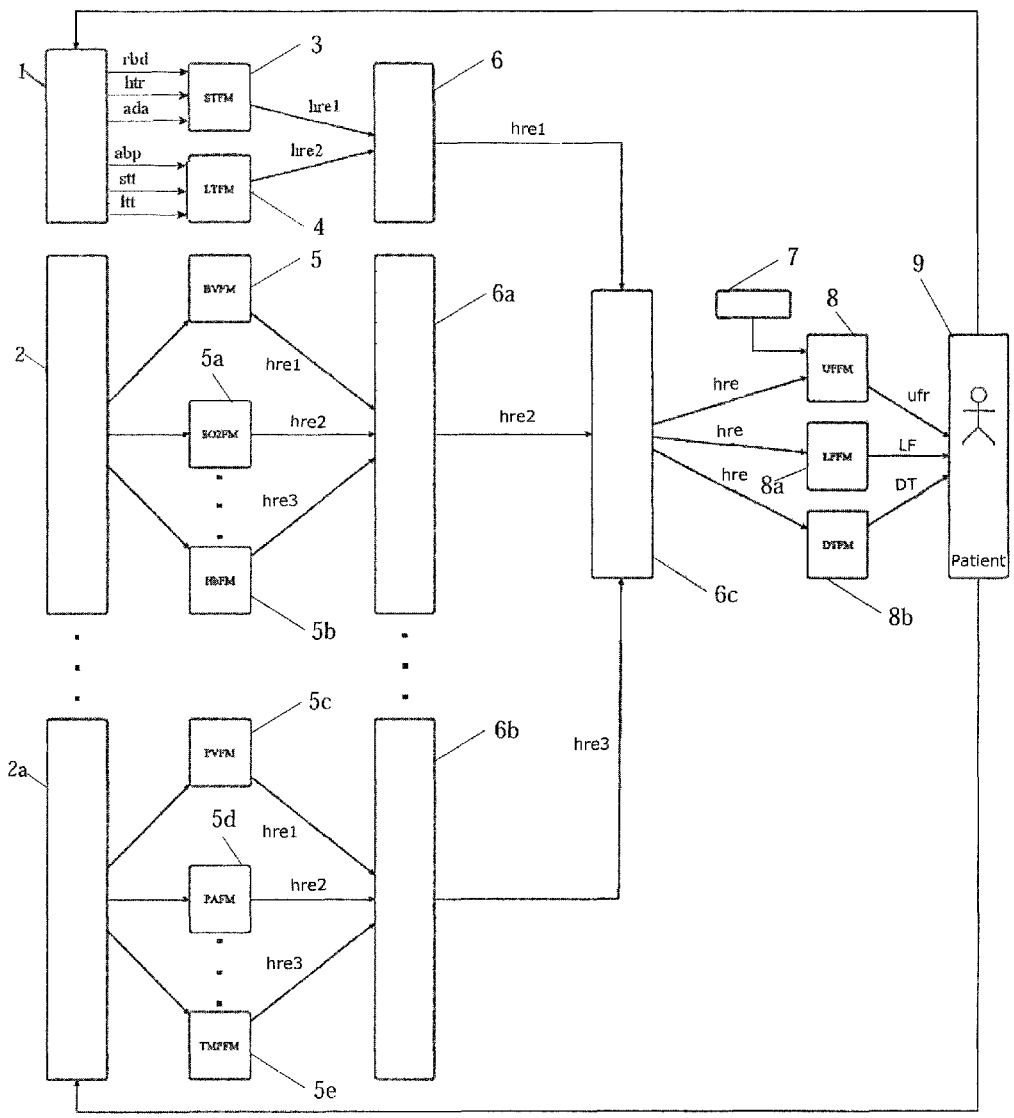
FIG. 12 shows another embodiment of the system according to the invention, FIG. 13 indicates a flow diagram of the blocks one and two of the system.

A possible extension of the physiological control loop is illustrated in FIG. 12.

The components 1 to 9 shown in FIG. 12 have been explained in the foregoing already by way of FIG. 1. The description there also applies to the embodiment according to FIG. 12 and consequently will not be repeated again.

In the embodiment according to FIG. 12 further modules are provided, namely an oxygen saturation fuzzy module 5a, a hemoglobin fuzzy module 5b, a fuzzy module 5c for the venous blood pressure, a fuzzy module 5d for the arterial blood pressure and a fuzzy module 5e for the transmembrane pressure. The fuzzy modules 5a, 5b receive their input parameters from the relative blood volume monitoring means 2. The fuzzy modules 5c to 5e receive their input values from machine sensors 2a detecting the arterial blood pressure, the venous blood pressure, the transmembrane pressure etc.

The embodiment according to FIG. 12 includes further weighting modules 6a, 6b and 6c in addition to the weighting module 6. The weighting module 6a performs a weighting of input parameters hre1, hre2, hre3 which are output from the fuzzy modules 5, 5a and 5b.

The weighting module 6b performs a weighting of input parameters hre1, hre2, hre3 which are generated by the fuzzy modules 5c, 5d and 5e, respectively. The weighting module 6c performs a repeated weighting of the weighted output parameters hre1, hre2, hre3 output by each of the weighting modules 6, 6a, 6b and transmits one or more weighted output signals hre to the fuzzy module 8 and, resp., to a dialysis fluid conductivity fuzzy module LFFM 8a and a dialysis fluid temperature fuzzy module DTFM 8b. Corresponding to the weighted output signals hre and the parameters output by the fuzzy modules 8, 8a and 8b, the dialysis fluid conductivity, the dialysis fluid temperature and/or the UF rate are set.

Hereinafter a simulation of the system will be explained. Here individual blocks containing the modules of the physiological control loop shown in FIG. 1 were simulated. The computed profiles of the UF rate are shown in the corresponding figures. The data used for simulation are real data of dialysis patients. The system shows in the UF profiles the response of the UF rate to the behavior of the blood pressure and the relative blood volume. Since in the simulation no control loop can be realized, no response of the blood pressure or the relative blood volume to the UF rate is given. There is only shown a response of the UF rate to the BP and the RBV course.

The following blocks of the physiological control loop include the following modules:

Block one: STFM 3 and UFFM 8,
Block two: LTFM 4 and UFFM 8,
Block three: BVFM 5 and UFFM 8,
Block four: STFM 3, LTFM 4, weighting module 6 and UFFM 8,
Block five: STFM 3, LTFM 4, BVFM 5, weighting module 6 and UFFM 8.

Figure 13:
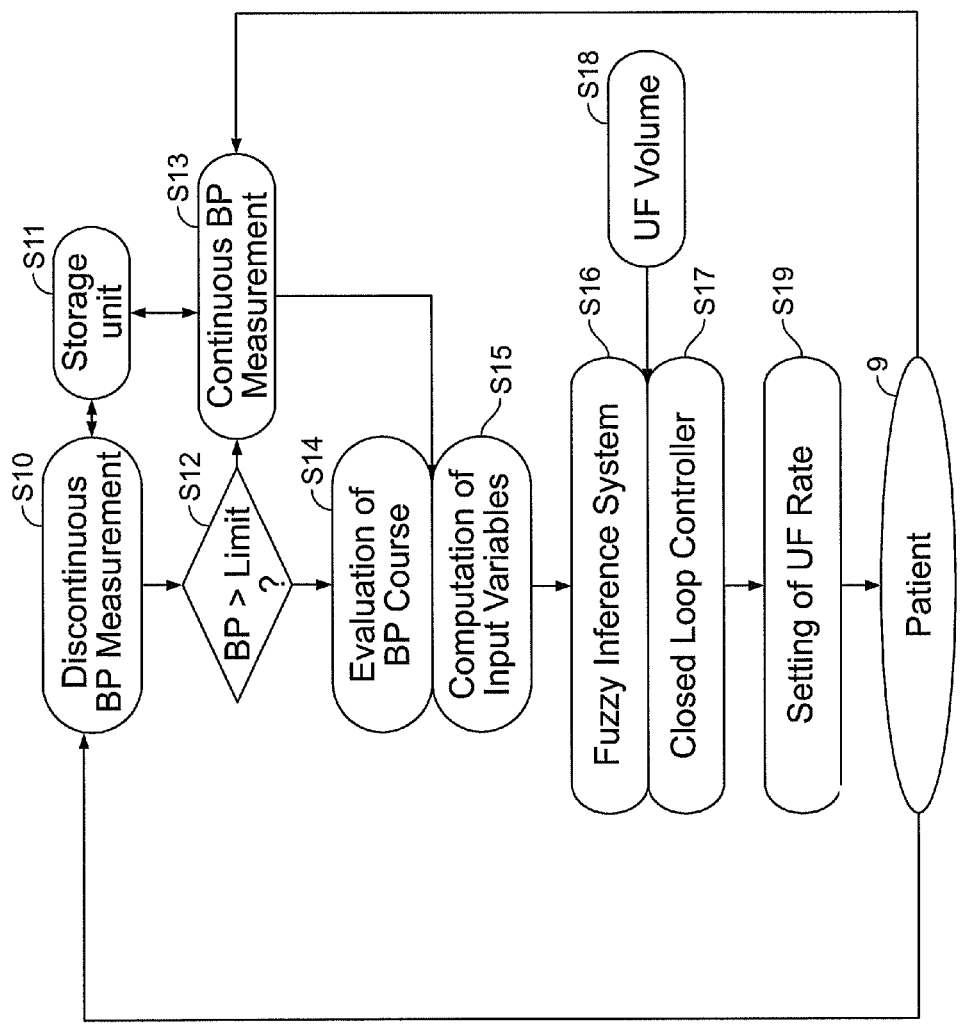

The flow diagram of the blocks one and two is shown in FIG. 13.

In the embodiment shown in FIG. 13 of a method lying within the scope of the present invention the functioning of the blocks one and two is explained. In step S10 a discontinuous blood pressure measurement is carried out, wherein the values obtained in this way can be stored in a storage unit S11 and then can be read out of the latter again. In step S12 it is checked whether or not the measured blood pressure exceeds the limit. When the limit has been exceeded, hereinafter a continuous blood pressure measurement is carried out in step S13 to obtain a more accurate quicker monitoring of the blood pressure and of the course of the blood pressure.

In step S14 the established course of the blood pressure is evaluated, i.e. either the discontinuously measured blood pressure according to the method step S10 or the continuously measured blood pressure according to the method step S13 (with a blood pressure exceeding the limit). In the following step S15 the input variables which are processed in a fuzzy inference system in step S16 are computed. In addition, the ultrafiltration volume (UF volume) can be established or taken into account in step S18.

In a control unit or control means with closed control loop at step S17 the respective matching ultrafiltration rate is established which then in step S19 is set as variable in the control loop. The patient 9 is treated with this ultrafiltration rate, i.e. the blood treatment is carried out so that the desired ultrafiltration rate is reached or at least approached.

Figure 14:
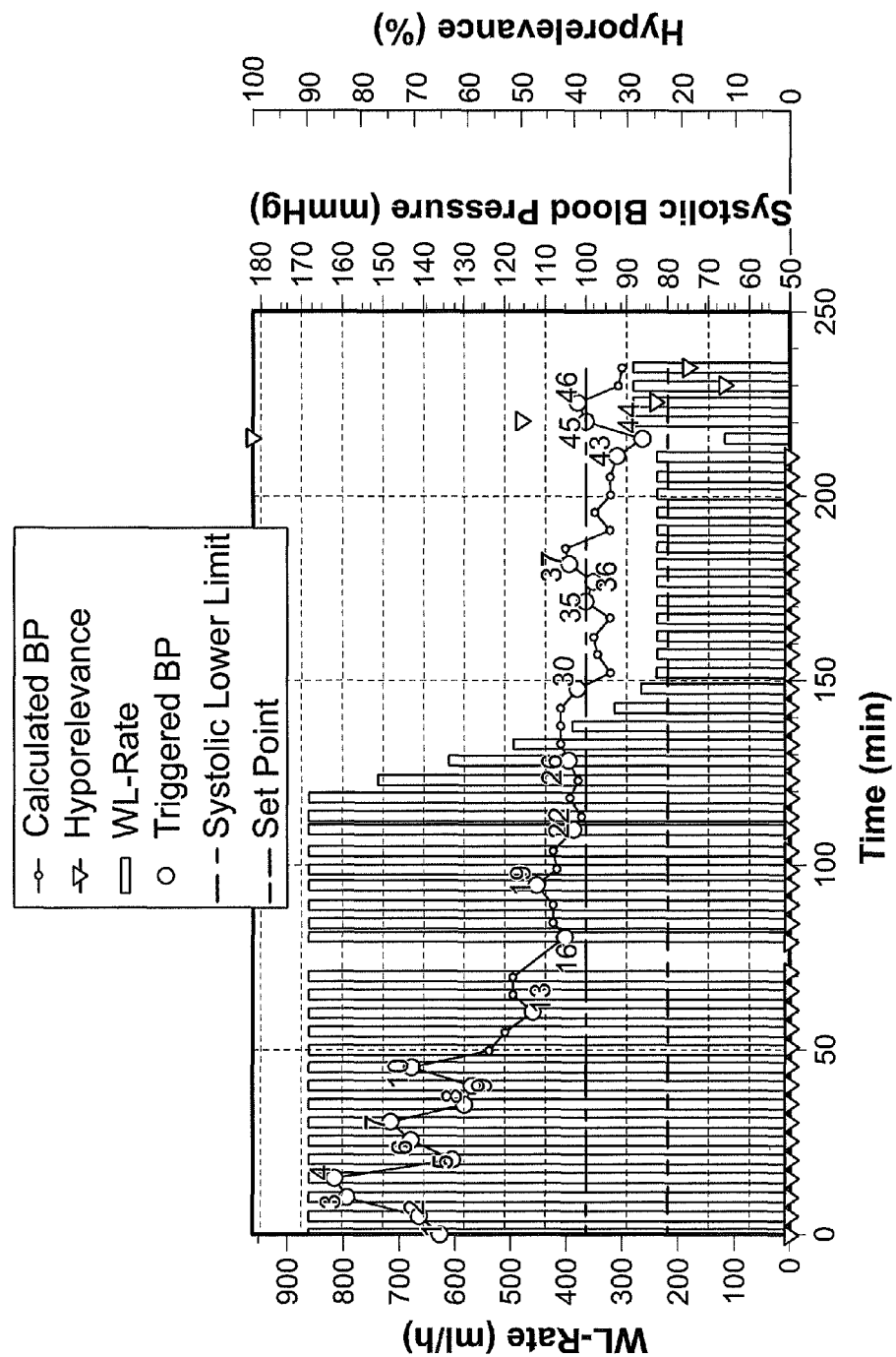
FIG. 14 shows simulation results of block one.

FIG. 14 represents a simulation of the first block and shows simulation results of block one. The STFM 3 evaluates variables which evaluate the blood pressure over a maximum of the last 30 minutes. The BP values consist of triggered and of computed BP values. When FIG. 13 is viewed at the 30 minutes interval, the blood pressure in these intervals shows no tendency to hypotension. Not before minute 220 does the blood pressure reach a systolic value of approx. 83 mmHg, which has resulted in a reduction of the UF rate.

Figure 15:
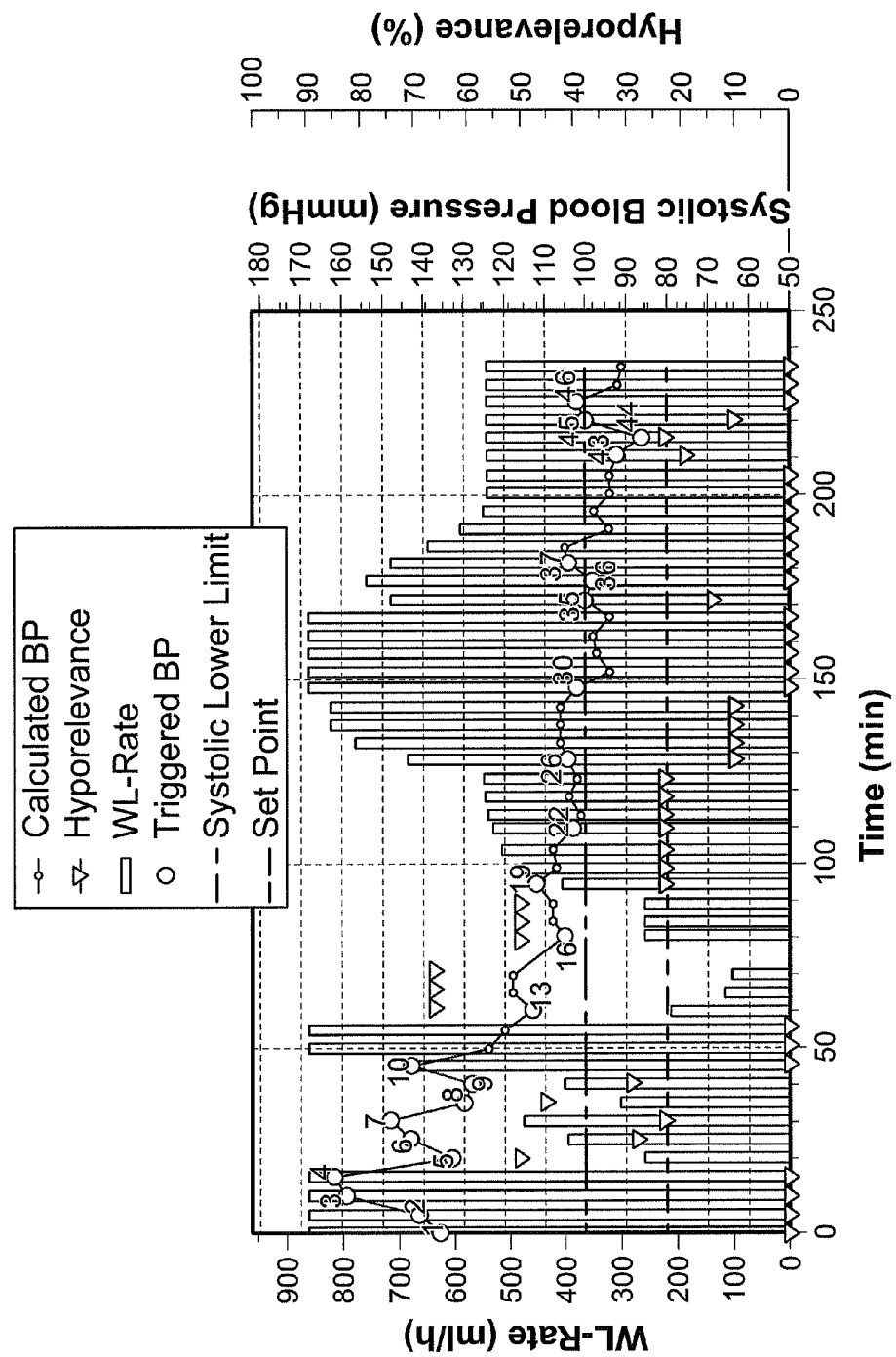
FIG. 15 illustrates simulation results of block two.
Figure 15:
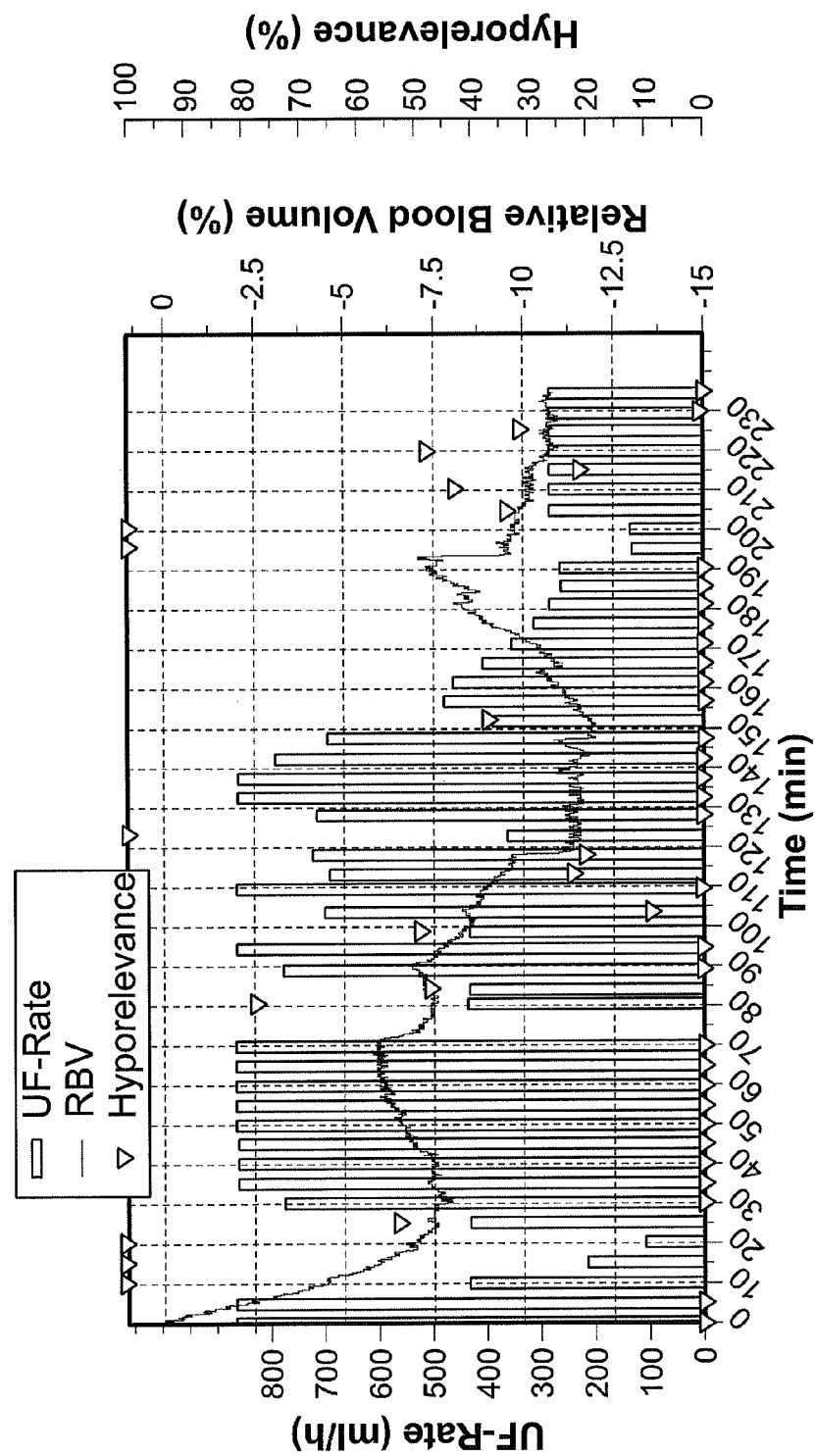

FIG. 15 represents a simulation of the second block, i.e. the modules LTFM 4 and UFFM 8, and hence shows simulation results of block two. The LFTM 4 only takes the triggered BP values into account. The input variables of this module include BP values that have been measured within the past 120 minutes. As shown in FIG. 15, the second module reacts more sensitively to BP variations than the STFM 3. A BP trend with decreasing blood pressure can be detected in good time, which results in a reduction of the UF rate in good time. This entails feedback in good time.

Figure 16:
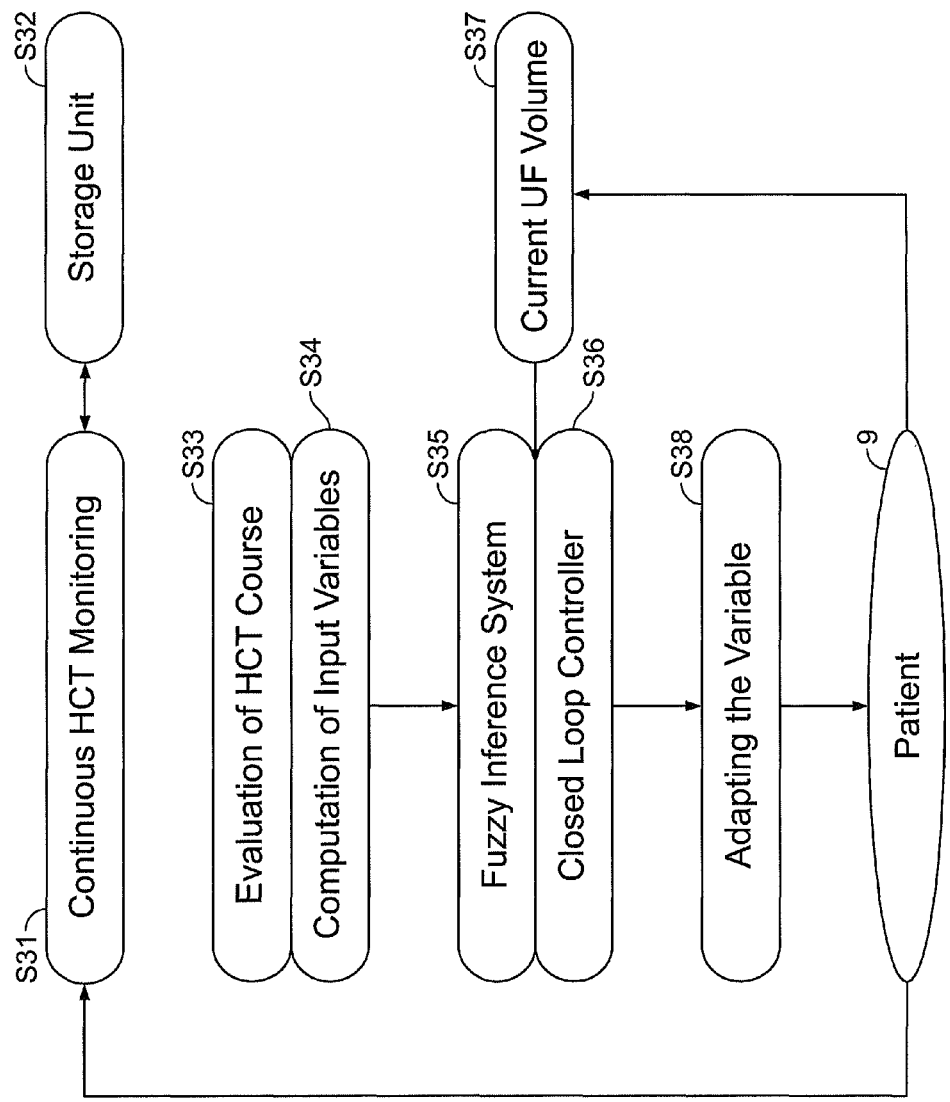
FIG. 16 shows a flow diagram of block three.

The flow diagram of block three is shown in the picture according to FIG. 16.

In FIG. 16 a flow diagram, i.e. an embodiment of a method is shown which is carried out according to block three. In step S31 continuous monitoring of one or more blood values is performed. In the embodiment according to FIG. 16 the hematocrit value (HCT) is continuously monitored. The measured values established during continuous blood value monitoring of step S31 are stored in a storage unit S32 which in one or several embodiments can be the same storage unit as the storage unit S11 according to FIG. 13. In step S33 the course of the blood values, especially the hematocrit course is evaluated. From this, input variables for a fuzzy module are computed which can be, for example, one of the fuzzy modules 5, 5a to 5e or another fuzzy module. The input variables computed in step S34 are supplied to a fuzzy inference system S35 that may have a closed loop controller S36. As a further input variable the controller S36 or the system S35 receives information about the current ultrafiltration volume which is continuously or intermittently monitored in step S37.

In step S38 the controller S36 carries out an adaptation of the variable by which the blood treatment of patient 9 is performed, i.e. the desired ultrafiltration rate is adapted.

Figure 17:
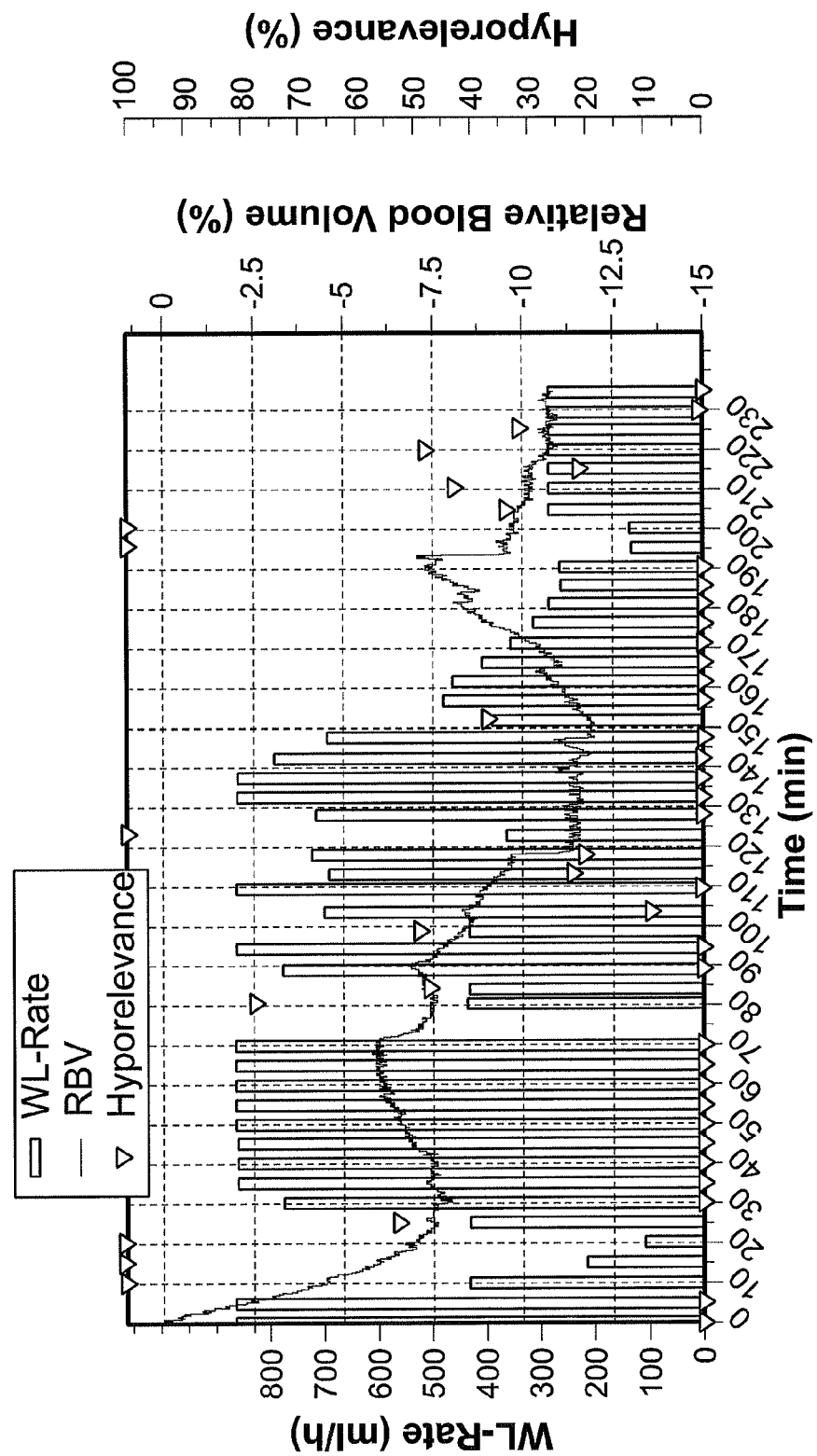
FIG. 17 illustrates simulation results of block three.
Figure 17:
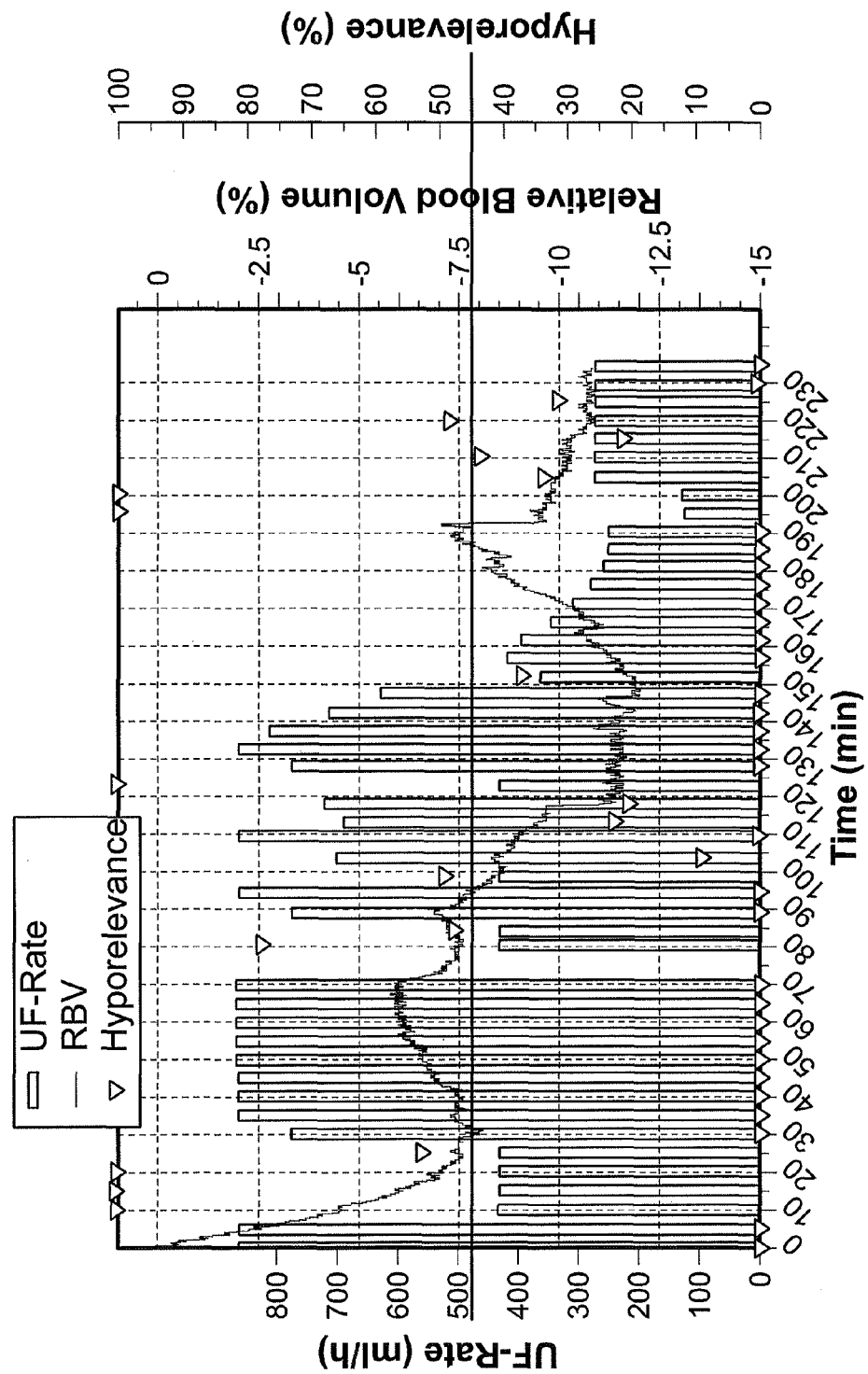

FIG. 17 illustrates simulation results of block three. The UF profile shown in FIG. 17 is intended to result in a control of the relative blood volume. The RBV is checked for gradients at intervals of 10 minutes with 50% overlapping. Depending on the intensity of a negative gradient the UF rate is reduced. In this way a stabilization of the relative blood volume is obtained which can result in a more stable condition of the patient.

Figure 18:
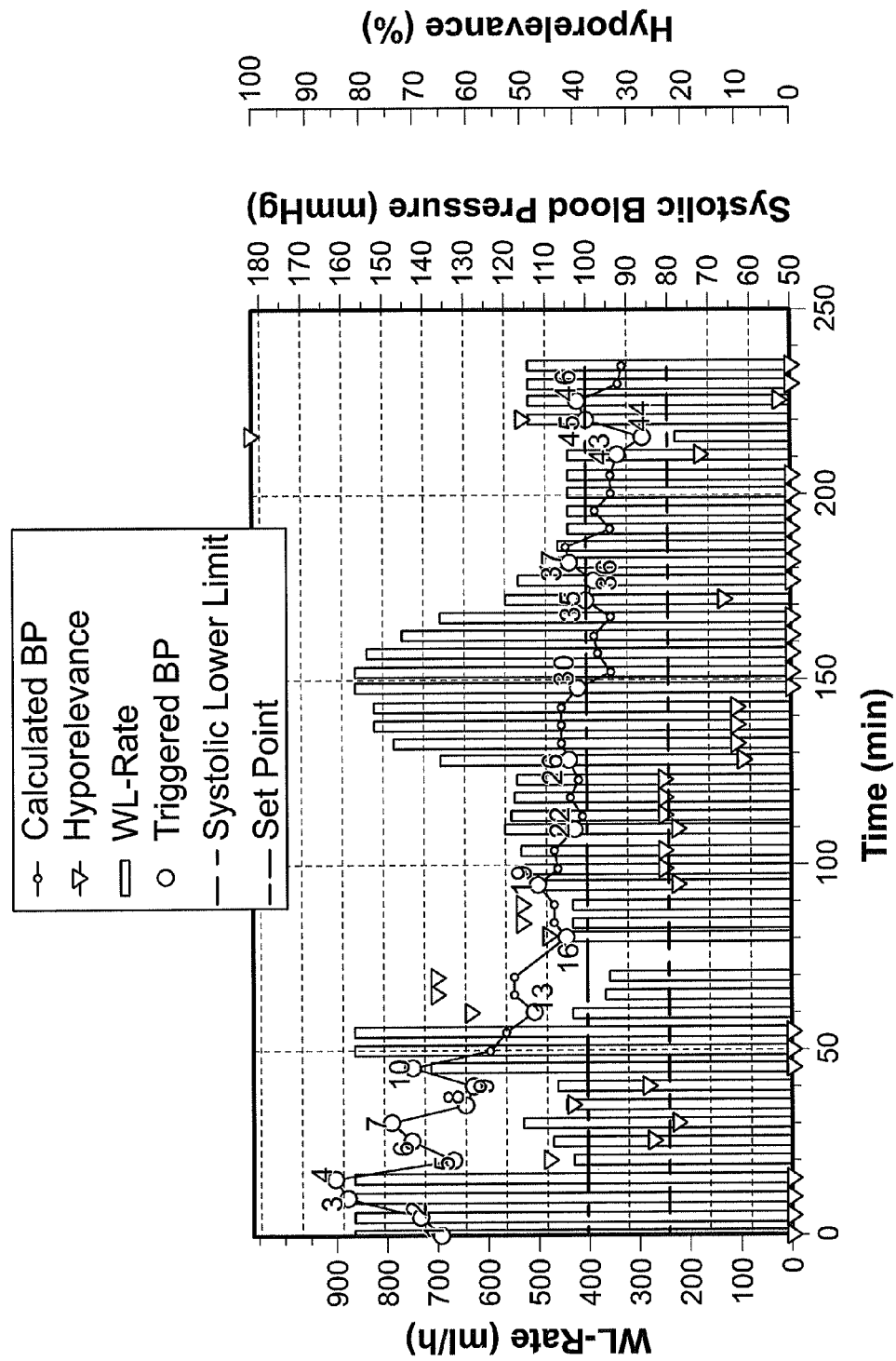
FIG. 18 shows simulation results of the combination of blocks one and two.

Also a simulation of STFM, LTFM and UFFM has been carried out. FIG. 18 shows simulation results for the modules STFM 3 and LTFM 4. FIG. 18 represents a simulation of the fourth block. In this block the STFM 3 and the LTFM 4 are implemented. Each of the modules computes a hyporelevance which are combined in weighting unit into a final hyporelevance. In this way two important pieces of information are supplied: The first indicates the behavior of the short time trend of the blood pressure including the computed BP values of the guideline technology. The STFM 3 also provides information about the distance of the last BP value from a preset BP safety limit upon exceeding of which the machine triggers an alarm. The second information is supplied by the LTFM 4 and includes an evaluation of the blood pressure over its long time behavior. These two pieces of information cover the behavior of the blood pressure over 120 minutes.

The reaction of the UF rate during simulation of the fourth block is similar to its reaction during simulation of the third block. A striking difference occurs at minute 215 where an UF rate reduction has taken place due to the STFM 3. This was not evident in the simulation of the third block.

Figure 19:
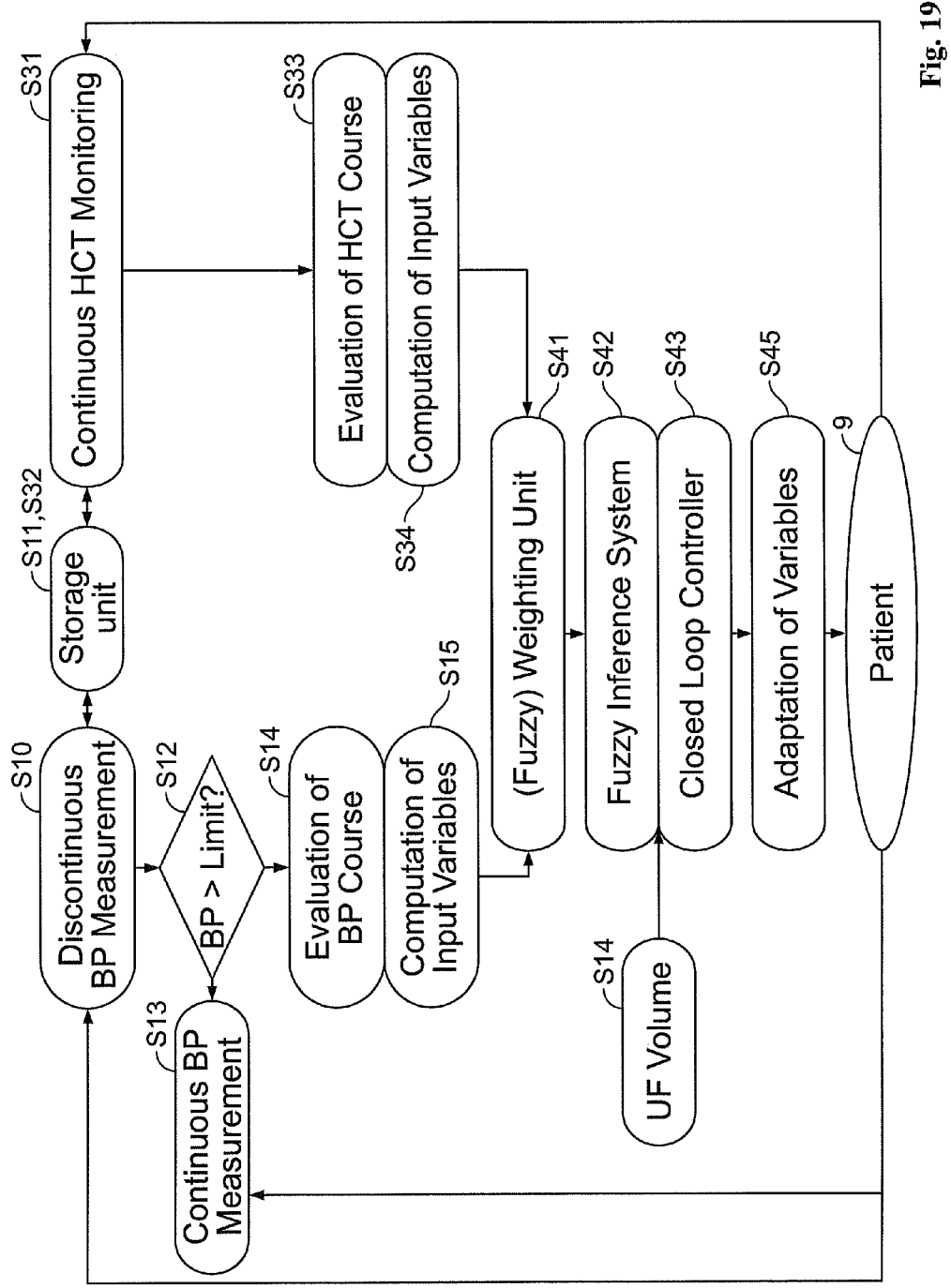
FIG. 19 shows an embodiment of a method according to the invention in the form of a flow diagram of the complete physiological control loop.

The flow diagram of the complete physiological control loop is represented in FIG. 19.

In FIG. 19 an embodiment of the complete physiological control loop according to an aspect of the invention is shown. The steps and features S10 to S15 shown in FIG. 19 correspond to the steps and features S10 to S15 already explained by way of FIG. 13. The storage unit S11 can simultaneously act as storage unit S32 shown in FIG. 16.

As is further illustrated in FIG. 19, the embodiment according to FIG. 19 also includes the steps and features S31 to S34 of the embodiment according to FIG. 16. In the embodiment according to FIG. 19, thus both a blood pressure measurement and a hematocrit monitoring are performed, wherein the blood pressure measurement can be carried out continuously or discontinuously. The hematocrit monitoring can equally be performed continuously or discontinuously. In the embodiment shown in FIG. 19 a discontinuous blood pressure measurement and a continuous hematocrit monitoring are taken as a basis.

In the embodiment according to FIG. 19, a weighting unit S41 is provided which can be a fuzzy module and which receives the values established for both the input variables computed in step S15 for the course of the blood pressure and the input variables computed in step S34 for the hematocrit course and weights them in response to internal, fixedly or variably predetermined weighting factors. The output variable output by the weighting unit S41 and formed on the basis of the course of blood pressure and hematocrit is supplied to a fuzzy inference system S42 also including a control means or, resp., a closed loop controller S43. Moreover, the established current ultrafiltration volume established in step S44 is supplied to the system S42 as input variable.

The controller S43 performs an adaptation of the variable S45 by which the blood treatment of patient 9 is carried out.

The steps or features S42 to S45 substantially correspond to the steps S16 to S19 of FIG. 13 or to the steps S35 to S38 of FIG. 16 with the special feature that the input variable for the fuzzy inference system S16 to S35 depends both on the course of the blood pressure and on the hematocrit course and that said two parameters are weighted and incorporated in the input signal of the fuzzy inference system S16 and S35, respectively.

Figure 20:
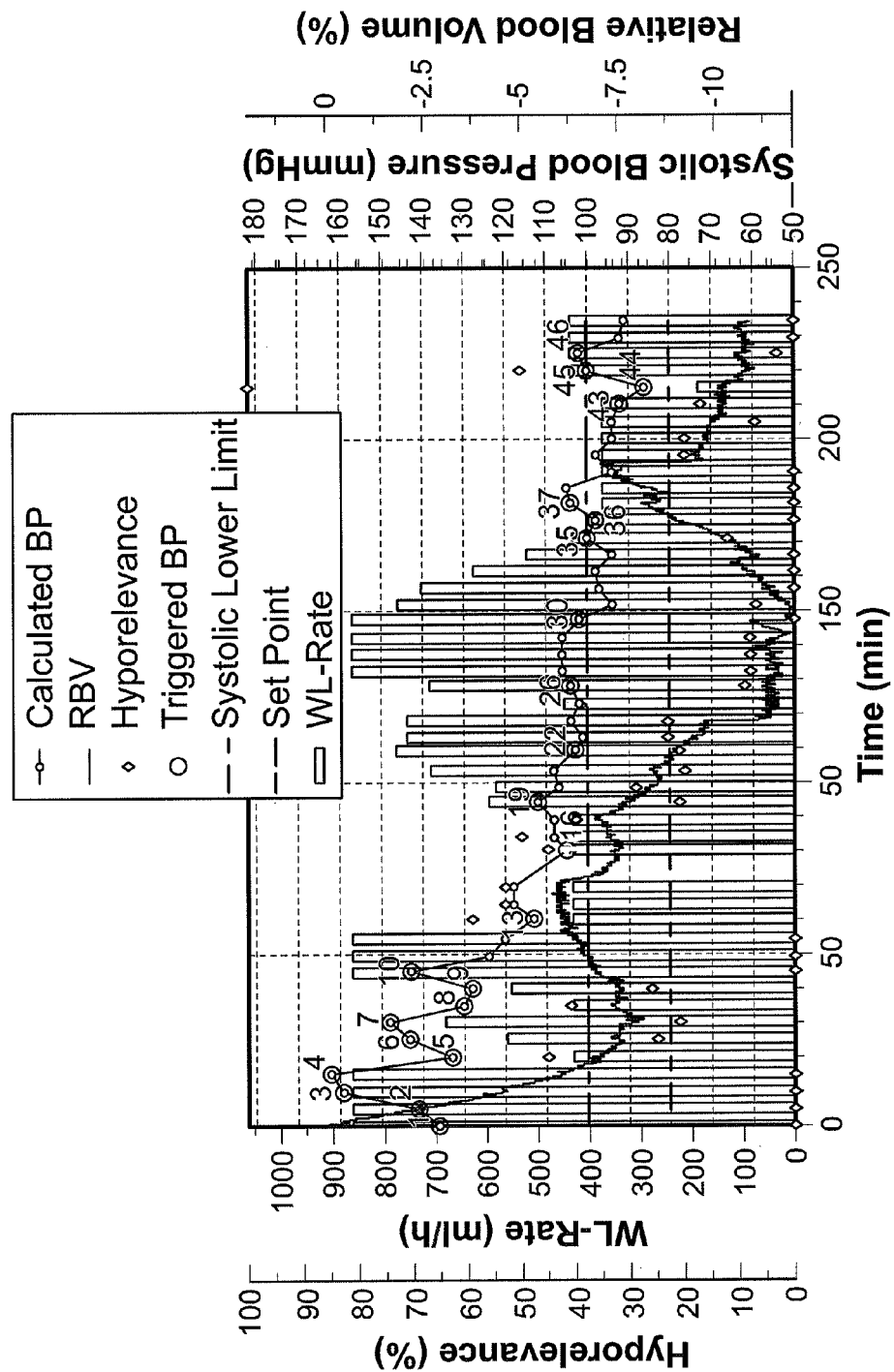
FIG. 20 shows simulation results of the entire system.

A simulation of STFM 3, LTFM 4, BVFM 5 and UFFM 8 was carried out. FIG. 20 simulates the complete physiological control loop. FIG. 20 shows all simulation results of the entire system. The UF rate profile represents a combination of all three input modules. Each modules computes, independently of the other modules, a hyporelevance that is combined into a final hyporelevance by a weighting unit. By this weighting a control of the variable dependent on the weightings is obtained, which results in a control of the input variables dependent on the weightings.

In one, several or all embodiments thus a novel physiological control loop is realized which includes at least two control parameters, viz. the blood pressure and the relative blood volume, which are processed in three or more different and independent fuzzy modules (STFM 3, LTFM 4 and BVFM 5). A weighting unit 6 combines the values issued from the three or more fuzzy modules and describing the condition of the patient by a value between 0 and 100% into final information about his/her condition. This information is processed together with the relative UF volume, which is the ratio of the current and the total UF volumes, in a further fuzzy module for computing the UF rate of the patient.

The invention claimed is:

1. A system for blood treatment which is configured to detect at least two hemodynamic parameters during the blood treatment, the system comprising:
   at least three fuzzy modules which receive measured values of the hemodynamic parameters as input variables, wherein each of the at least three fuzzy modules forms a respective output value (hre1, hre2, hre3), each of the respective output values representing a hypotonic relevance status variable;
   at least one weighting module to which a plurality of output signals transmitted by the at least three fuzzy modules are supplied, wherein the weighting module is configured to combine the respective output values hre1, hre2, and hre3 formed by the at least three fuzzy modules into a resulting output value;
   a further fuzzy module configured to evaluate the resulting output value together with a relative ultrafiltration volume, such that the evaluation at least one of describes a ratio between a current and a total ultrafiltration volume or evaluates a relative time, which describes a ratio between a current and a total time;
   wherein the further fuzzy module computes and sets at least one of a corresponding desired ultrafiltration rate, dialysis fluid conductivity, or dialysis fluid temperature, in response to an output signal transmitted by the weighting module.

2. The system according to claim 1, configured to detect or avoid intradialytic hypotensive episodes and in which the hemodynamic parameters monitored comprise two or more of the following parameters:
   blood pressure, course of blood pressure, relative blood volume, course of relative blood volume, hematocrit value, hematocrit course, oxygen saturation, course of oxygen saturation of the blood, heart rate, course of heart rate,
   absorbance of uremic toxins or hemodynamic courses, or,
   physical parameters or physical courses including blood pressure values measured by the system, the blood pressure values including at least one of arterial blood pressure, venous blood pressure, course of arterial blood pressure, or course of venous blood pressure.

3. The system according to claim 1, which is designed as a dialyzer for hemodialysis, hemofiltration or hemodiafiltration.

4. The system according to claim 1, which is configured to discontinuously measure blood pressure values at predetermined irregular time intervals, to compare them to a limit and, in the case of decrease of the blood pressure value below the limit, to change to continuous blood pressure measurement.

5. The system according to claim 1, in further comprising a short time fuzzy module configured to
   measure blood pressure values at different time intervals, compared the measured blood pressure values to a limit,
   evaluate the behavior of the blood pressure at an earlier time period comprising one or more particular earlier time intervals at which the blood pressure values were measured, and
   compute a variable reflecting the patient's condition by evaluating rules or fuzzy rules.

6. The system according to claim 5, further comprising a long time fuzzy module configured to evaluate a course of the blood pressure is evaluated after curve adaptation or by using an algorithm, including a linear least square algorithm, over an earlier period of time comprising one or more particular earlier time intervals at which blood pressure values were measured, the earlier period of time which is longer than the period of time evaluated by the short time fuzzy module.

7. The system according to claim 1, comprising a measuring unit in the form of a hemosensor and a further fuzzy module configured to evaluate the measuring signal transmitted by the hemosensor and to evaluate the blood volume and the course of the blood volume of a patient.

8. The system according to claim 1, wherein the course of a relative blood volume (RBV) is stored in the form of a RBV curve, the RBV curve having different time window sizes is estimated by an algorithm, and the course of the blood volume is monitored at time intervals corresponding to a time window having a temporal size during which 50% or more overlaps to result in the actual course of the blood volume.

* * * * *